(12) United States Patent
Farrell et al.

(10) Patent No.: US 8,784,348 B2
(45) Date of Patent: *Jul. 22, 2014

(54) SPLINT ASSEMBLY FOR POSITIONING OF THE HAND

(75) Inventors: John F. Farrell, Morehead, NC (US); Henry Hoffman, Charlotte, NC (US)

(73) Assignee: Saebo, Inc., Charlotte, NC (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/311,222

(22) Filed: Dec. 5, 2011

(65) Prior Publication Data

US 2012/0078150 A1    Mar. 29, 2012

Related U.S. Application Data

(63) Continuation of application No. 12/251,273, filed on Oct. 14, 2008, now Pat. No. 8,070,702.

(60) Provisional application No. 60/979,351, filed on Oct. 11, 2007.

(51) Int. Cl.
A61F 5/00 (2006.01)
A63B 23/14 (2006.01)

(52) U.S. Cl.
USPC ............ 602/21; 602/5; 602/20; 486/46

(58) Field of Classification Search
CPC .................................. A61F 5/00; A63B 23/14
USPC ........... 602/4–6, 60–64, 16, 20–22; 128/878, 128/879, 882, 877, 880, 881; 482/45–46
See application file for complete search history.

(56) References Cited

U.S. PATENT DOCUMENTS

| | | | |
|---|---|---|---|
| 3,256,880 A * | 6/1966 | Caypinar | 128/877 |
| 3,631,542 A | 1/1972 | Potter | |
| 4,485,808 A | 12/1984 | Hepburn | |
| 4,508,111 A | 4/1985 | Hepburn | |
| 4,538,600 A | 9/1985 | Hepburn | |
| 4,772,012 A | 9/1988 | Chesher | |
| 4,798,199 A * | 1/1989 | Hubbard et al. | 602/21 |
| 4,944,290 A | 7/1990 | Hepburn | |
| 4,947,838 A | 8/1990 | Giannetti | |
| 4,960,114 A | 10/1990 | Dale | |
| 4,977,890 A | 12/1990 | Mann | |
| 5,056,504 A | 10/1991 | Mann | |
| 5,203,766 A | 4/1993 | Carter et al. | |
| 5,295,948 A | 3/1994 | Gray | |
| 5,520,625 A | 5/1996 | Malewicz | |
| 5,558,624 A | 9/1996 | Hepburn | |
| 5,921,945 A | 7/1999 | Gray | |

(Continued)

OTHER PUBLICATIONS

Available Neurological Dynasplint Systems.

*Primary Examiner* — Patricia Bianco
*Assistant Examiner* — Ophelia A Hawthorne
(74) *Attorney, Agent, or Firm* — Nelson Mullins Riley & Scarborough, LLP

(57) ABSTRACT

A hand splint includes a forearm component, a strut mounted on the forearm component, and a hand component mounted on the strut such that a spacing is defined between the hand component and the forearm component. The hand component is configured to receive the volar surface of at least one of the digits of a user's hand and may include a resilient section for generating a continuous restoring force in response to bending.

20 Claims, 17 Drawing Sheets

(56) References Cited

U.S. PATENT DOCUMENTS

| 6,506,172 | B1 | 1/2003 | Hepburn |
| 6,942,629 | B2 | 9/2005 | Hepburn |
| 7,001,352 | B2 | 2/2006 | Farrell |
| 7,081,102 | B1 * | 7/2006 | Koetter et al. ............ 602/21 |
| 7,547,290 | B1 * | 6/2009 | Al-Oboudi ............... 602/21 |

* cited by examiner

SPLINT ASSEMBLY FOR POSITIONING OF THE HAND

CROSS-REFERENCE TO RELATED APPLICATIONS

The present application is a continuation of U.S. patent application Ser. No. 12/251,273, filed Oct. 14, 2008, now U.S. Pat. No. 8,070,702, which is a nonprovisional patent application of, and claims priority under 35 U.S.C. §119(e) to, U.S. Provisional Patent Application Ser. No. 60/979,351, filed on Oct. 11, 2007, which patent applications are incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

FIELD OF THE INVENTION

The invention generally relates to orthoses and, in particular, to splint assemblies for the hand.

BACKGROUND OF THE INVENTION

Often following a neurological injury one or both of the upper extremities are affected with hemiparsis. Hemiparsis is a condition wherein the arm and hand no longer function as they should, and the patient is unable to use or has decreased use of the affected arm and hand. If this condition is not addressed at the onset with a positioning splint, the fingers usually rest in a curled or fisted position. The curled position leads to soft tissue shortening of the long finger flexors (FDS & FDP). Soft tissue shortening often results in contracture of these muscles, which leads to decreased range of motion at the wrist and finger joints. Specifically, a contracture is a shortening of a muscle or tendon in the body in response to stress exerted on that muscle or tendon. As the soft tissue shortening begins and when the patient becomes more active, two other conditions may occur, hypertonicity and spasticity. These conditions will usually pull a person's fingers into a closed first thereby further increasing soft tissue shortening.

Many current splint designs position the user's wrist and hand in varying degrees of flexion with the goal being extension. This positioning is used in order to help prevent or correct muscle contracture. In the case of a chronic hand, splints can usually be positioned to accommodate the hand's current length depending on soft tissue shortening, and gradually be adjusted in varying degrees of extension to help provide a low load, long duration stretch to the long finger flexors.

Many current splint designs have a combined forearm and hand section and are either volar or dorsal based. Sometimes they will be dorsal based at the forearm and volar based at the hand. Other designs offer a forearm section and a separate hand piece. These designs are joined together at the wrist with one or two outriggers or struts, typically with a hinge mechanism on one or both sides of the wrist. These hinges are either static progressive or dynamic in nature. The struts that connect the forearm and hand piece via the wrist hinge are usually on both the ulnar and radial sides, however there may be only one on one side. The static progressive hinge component can be adjusted over time, in varying degrees of flexion/extension, and does not offer a continuous force in extension. This allows the health care professional to start at the patient's current position and move in incremental units towards extension as the soft tissue stretches.

Some splint models offer a dynamic hinge that can be adjusted to put a desired amount of continuous tension toward extension to help facilitate the wrist and fingers in an extended position with a low load, long duration stretch.

Improvements to available designs are needed with regard to the static hand piece. More particularly, as a dynamic neurologically-impaired hand is affected with hypertonicity and spasticity, a patient's fingers tend to want to move into a flexed or fisted position. However, the splint forces the hand to stay in an outstretched position thereby causing the hand to continue to move into flexion against the static hand piece. Often the joints in the fingers of the hand are damaged or deformed because the hand continues to contract against the rigid splint. Thus, joint deformities of the fingers are a common problem when splinting the dynamic neurologically-impaired hand, using a static hand piece.

A dynamic splint that may address one or more of these concerns is disclosed in International Patent Application No. PCT/US2005/047600 which published on Jul. 6, 2006 as WO/2006/072068; and in U.S. Patent Application Publication No. 2007/0055191 which published on Mar. 8, 2007, both of which are incorporated herein by reference. The splint assembly of the present invention represents new variations in the embodiments of the splints disclosed in these two patent references.

SUMMARY OF THE INVENTION

The invention includes many aspects and features. Moreover, while many aspects and features relate to, and are described in, the context of a hand splint assembly, the present invention is not necessarily limited to use only in hand splint assemblies.

In a first aspect of the invention, a hand splint includes: a forearm component configured to attach to a person's forearm such that a distal end of the forearm component is located proximate the person's wrist and such that the forearm component extends up the person's arm; a hand component configured to receive, in supporting abutment therewith, a volar surface of the thumb and digits 2 through 5 of the person's hand; and a palm support component coupling together the forearm component and the hand component. The palm support component in turn includes: an adjustable hinge attached to the forearm component such that, when the forearm component is attached to the forearm, the adjustable hinge is located adjacent the person's carpals whereas the wrist normally flexes and extends; a palm support platform; and a strut attached to and coupling together the adjustable hinge and the palm support platform. The palm support platform is mounted to the hand component beneath an area of the hand component that is configured to receive, in supporting abutment therewith, a volar surface of the palm of the hand. The strut extends from the forearm component such that a spacing is defined between the hand component and the forearm component, whereby the strut spans the wrist of the person when the hand splint is donned. Adjustment of the adjustable hinge adjust the orientation and spacing of the palm support platform relative to the forearm component. A portion of the hand component is malleable such that the portion of the hand component may be bent for customizing the abutting support of the hand by the hand component.

In a feature of this aspect of the invention, the malleable portion includes at least the area of the hand component configured to receive the volar surface of the palm of the hand.

In a feature of this aspect of the invention, the malleable portion includes at least the area of the hand component configured to receive the volar surface of the thumb and the volar surface of the palm of the hand.

In a feature of this aspect of the invention, the hand splint further includes a second strut and a second adjustable hinge mounted to the forearm component. The second strut is attached to and couples together the second adjustable hinge and the palm support platform. The second strut extends on an opposite side of the forearm component relative to the first strut.

In a feature of this aspect of the invention, the malleable portion includes at least the area of the hand component configured to receive the volar surface of the thumb.

In a feature of this aspect of the invention, the hand component includes a generally curved, semi-cylindrical portion that is rigid, and the hand component is configured to receive in supporting abutment therewith the volar surface of the thumb and the volar surface of digits 2 through 5 of the hand when the hand is in a fisted position, the generally curved, semi-cylindrical portion receiving in supporting abutment therewith the volar surface of digits 2 through 5 when flexed in the fisted position of the hand.

In a feature of this aspect of the invention, the malleable portion includes the area of the hand component configured to receive the volar surface of the thumb, the volar surface of digits 2 through 5, and the volar surface of the palm of the hand.

In a feature of this aspect of the invention, the hand component includes a generally curved portion that is malleable, and the hand component is configured to receive in supporting abutment therewith the volar surface of the thumb and the volar surface of digits 2 through 5 of the hand when the hand is in an intermediate position generally midway between a fisted position and a fully open position, the generally curved portion of the hand component including a generally curved surface for engagement with digits 2 through 5 when partially flexed in the intermediate position of the hand.

In a feature of this aspect of the invention, neither the forearm component nor the hand component is configured to span the wrist when the hand splint is donned.

In another aspect of the invention, the hand splint includes a forearm component that is configured to attach to a person's forearm such that a distal end of the forearm component is located proximate the person's wrist and such that the forearm component extends up the person's arm; a hand component having a first section configured to receive, in supporting abutment therewith, a volar surface of both the palm and thumb of the hand, and a second section configured to receive, in supporting abutment therewith, a volar surface of digits 2 through 5 of the person's hand, the first and second sections being removably secured to one another; and a strut attached to and coupling together the forearm component and the hand component, the strut extending from the forearm component such that a spacing is defined between the hand component and the forearm component, whereby the strut spans the wrist of the person when the hand splint is donned. The first section of the hand component comprises a malleable material that does not generate, in response to bending, a continuous restoring force in opposition to such bending, whereby the second section is able to be manually shaped for customizing the abutting support of the hand by the second section of the hand component. The second section of the hand component comprises a resilient material that, in response to bending, such as during flexion of an abutted finger, generates a continuous restoring force in opposition to such bending, whereby an abutted finger in flexion is urged toward extension.

In a feature of this aspect of the invention, the hand splint further includes a second strut and a second adjustable hinge mounted to the forearm component. The second strut is attached to and couples together the second adjustable hinge and the palm support platform, and the second strut extends on an opposite side of the forearm component relative to the first strut.

In a feature of this aspect of the invention, the second section of the hand component is configured to abut the volar side of the length of at least one of digits 2 through 5.

In a feature of this aspect of the invention, the second section is releasably connected to the first section such that the second section may be readily substituted with another section comprising a material having a different resiliency relative to the second section.

In a feature of this aspect of the invention, the hand splint further includes a plurality of straps for securing the hand component to a hand, and the second section of the hand component defines a slot having an extent sufficient for three of the straps to concurrently extend there through.

In a feature of this aspect of the invention, the hand splint further includes a plurality of straps for securing the hand component to a hand, and at least one of the straps comprises a non-slip material on a volar side thereof for frictional engagement with the skin of the hand and digits.

In a feature of this aspect of the invention, the hand splint further includes a plurality of straps for securing the hand component to a hand, and the second section defines a side indentation along an ulnar side thereof for receipt and retention therein of one of the straps when wrapped around the ulnar side of the second section, the strap configured for wrapping around digit 5 of the hand.

In a feature of this aspect of the invention, the hand splint further includes a plurality of straps for securing the hand component to a hand, and the hand component defines a side indentation along a radial side thereof for receipt and retention therein of at least one of the straps when wrapped around the radial side of the second section, the strap configured for wrapping around digit 2 of the hand.

In a feature of this aspect of the invention, the hand splint further includes a plurality of straps for securing the hand component to a hand, and the first section and the second section of the hand component, when connected together, define a side indentation along an ulnar side of the hand component for receipt and retention therein of one of the straps when wrapped around the ulnar side of the hand component, the strap configured for wrapping around the palmer portion and the dorsum of the hand.

In a feature of this aspect of the invention, the hand splint further includes a plurality of straps for securing the hand component to a hand, and the second section defines side indentations along opposite sides thereof for receipt and retention therein of one of the straps configured for wrapping around the thumb of the hand.

In another aspect, a hand splint includes: a forearm component configured to attach to a person's forearm such that a distal end of the forearm component is located proximate the person's wrist and such that the forearm component extends up the person's arm; a hand component having a first section configured to receive, in supporting abutment therewith, a volar surface of the palm of the hand; a second section configured to receive, in supporting abutment therewith, a volar surface of digits 2 through 5 of the person's hand; and a third section configured to receive, in supporting abutment therewith, a volar surface of the thumb of the hand, the first, second and third sections being removably secured to one another; and a strut attached to, and coupling together, the forearm component and the hand component, the strut extending from the forearm component such that a spacing is defined between the hand component and the forearm component, whereby the strut spans the wrist of the person when the hand splint is donned. The first section of the hand component comprises a malleable material that does not generate, in response to bending, a continuous restoring force in opposition to such bending, whereby the first section is able to be manually shaped for customizing the abutting support of the hand by the first section of the hand component. The second section of the hand component comprises a resilient material that, in response to bending, such as during flexion of an abutted one of digits 2 through 5 of the hand, generates a continuous restoring force in opposition to such bending, whereby an abutted digit in flexion is urged toward extension. The third section of the hand component comprises a resilient material that, in response to bending, such as during flexion of the thumb, generates a continuous restoring force in opposition to such bending, whereby an abutted thumb in flexion is urged toward extension.

In yet another aspect, a hand splint includes a forearm component configured to mount on a person's forearm that starts proximate a person's wrist and extends up a person's arm several inches; a strut mounted on a lateral side of the forearm component; and a volar hand component mounted on the strut such that a spacing extends between the volar hand component and the forearm component, whereby the strut spans a wrist of the person when the hand splint is worn. The hand component is configured to receive in supporting abutment therewith the volar surface of digits 2 through 5 of the person's hand.

In a feature of this aspect of the invention, the hand component is further configured to receive in supporting abutment therewith the volar surface of the thumb of the hand.

In a feature of this aspect of the invention, the hand component is further configured to receive in supporting abutment therewith the volar surface of the palm of the hand.

In a feature of this aspect of the invention, the hand component is removably mounted to the strut.

In a feature of this aspect of the invention, the hand splint further includes a second hand component that is interchangeable with the first hand component and is configured to be removably mounted to the strut.

In another aspect, a hand splint includes a forearm component that starts proximate a person's wrist and extends up a person's arm several inches; and a hand component coupled to the forearm component, the hand component covering the volar surface of the thumb of the person's hand and digit 2 through digit 5 of the hand and comprising sections constructed of different materials, including a first section constructed from a first material that is primarily static in nature when the splint is worn and a second section constructed from a second material that is made of an energy storing material (e.g., an elastic or spring-like material that permits bending and provides a restoring force when bent), the energy storing material of the second section allowing the fingers and the joints thereof (MCP, PIP, and/or DIP) to move through flexion as the hand moves into a flexed or fisted position (resulting from tone, spasticity, and postural changes) and then be urged back into an extended position by the energy storing properties of the material.

In a feature of this aspect of the invention, the hand component is not configured to span the wrist.

In a feature of this aspect of the invention, neither the first, second, nor third sections forms part of the forearm component.

In a feature of this aspect of the invention, neither the forearm component nor the hand component is configured to span the wrist.

In a feature of this aspect of the invention, the first section is malleable so as to position and contour the first material as desired for intimate fit on the hand.

In a feature of this aspect of the invention, the hand component further comprises a thumb section, the first section extending between the second section and the thumb section.

In a feature of this aspect of the invention, the hand component further comprises a thumb section, the second section being separate and distinct from the thumb section.

In a feature of this aspect of the invention, the thumb section is static.

In a feature of this aspect of the invention, the thumb section is dynamic.

In a feature of this aspect of the invention, the hand component includes a dynamic thumb section made of the energy storing material of the second section.

In a feature of this aspect of the invention, the second section begins proximate the MCP joint of the thumb and runs to the tip of the thumb.

In a feature of this aspect of the invention, a palm support component couples together the hand component and the forearm component.

In addition to the aforementioned aspects and features of the invention, it should be noted that the invention further includes: the various possible combinations of such aspects and features; methods of exercising a hand using a splint assembly in accordance with any of the foregoing aspects; methods of protecting a hand using a splint assembly in accordance with any of the foregoing aspects; and methods of making a splint assembly in accordance with any of the foregoing aspects.

BRIEF DESCRIPTION OF THE DRAWINGS

One or more preferred embodiments of the invention now will be described in detail with reference to the accompanying drawings, which are for the purpose only of illustrating dynamic splint assemblies and components thereof and are not intended to be to scale.

DETAILED DESCRIPTION OF THE INVENTION

Figure 1:
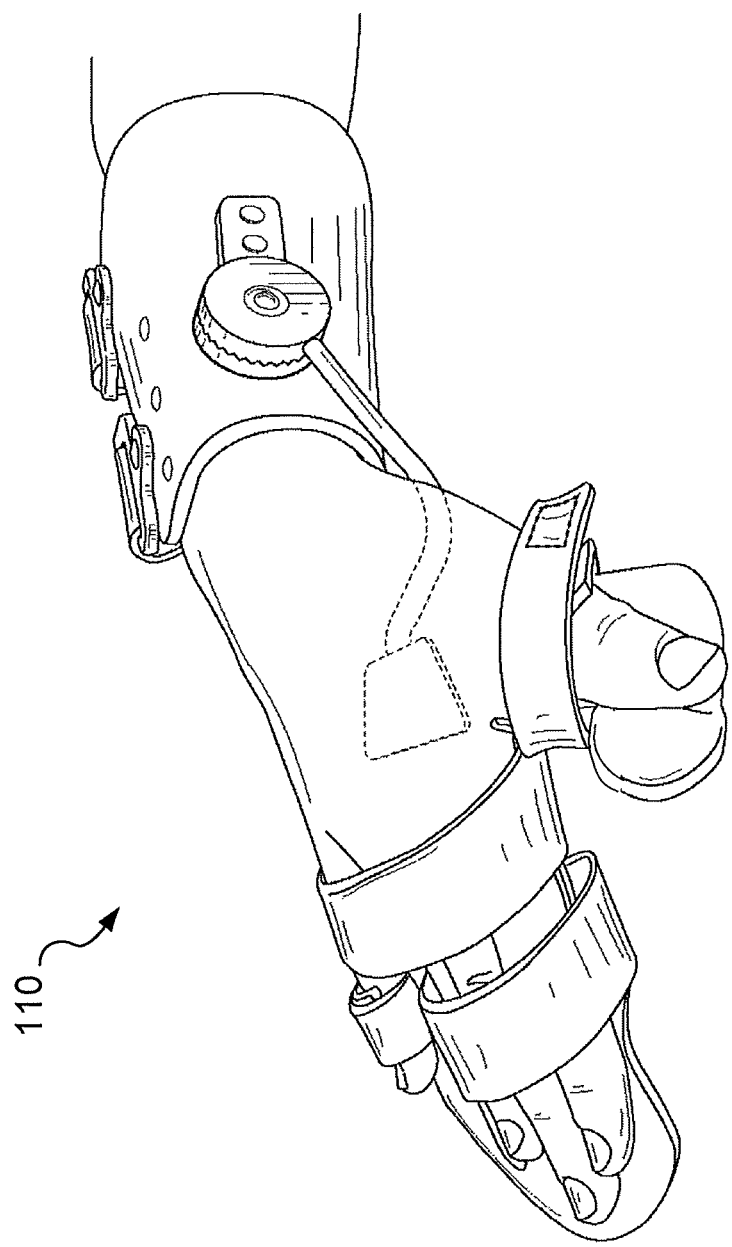
FIG. 1 is a perspective view of a first splint assembly 110 in accordance with a preferred embodiment of the invention, wherein the splint assembly is worn on a person's right hand.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Moreover, many embodiments, such as adaptations, variations, modifications, and equivalent arrangements, will be implicitly Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein-as understood by the Ordinary Artisan based on the contextual use of such term-differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, several terms such as "dorsal," "volar," "radial," and "ulnar" are used herein with reference to features of the human hand. Indeed, descriptions herein of one or more illustrated embodiments of the invention sometimes are made with such terms that may imply that the embodiment is disposed on a forearm and hand. Use of such terms of reference is made herein in order to facilitate an understanding of the invention, and the forearm and the hand are not considered in such embodiments to be actual elements of the invention.

Moreover, for the purpose of interpreting these terms of reference, the reader should consider a forearm and open hand resting palm-side down upon a planar desktop, with the forearm and palm generally contacting the desktop, and with the fingers and thumb generally straight and resting their lengths on the desktop. The volar sides of the forearm, wrist, hand, and fingers are generally disposed toward and contact the desktop. Thus, the fingerprints generally are found on the volar sides of fingertips. The dorsal sides of the forearm, wrist, hand, and fingers generally face in opposite direction to the volar sides of the forearm, wrist, hand, and fingers. These dorsal sides thus would be generally oriented away from the desktop. For example, fingernails generally grow from the dorsal sides of the fingers. The side of the hand from which the thumb depends defines the radial side of the forearm, wrist, and hand. In contrast, the side of the hand opposing the radial side defines the ulnar side of the forearm, wrist, and hand. For example, the fourth finger from the thumb of the hand, generally the smallest finger often called the "pinkie" finger, depends from the ulnar side of the hand. In view of these clarifications, these terms of reference are unambiguous and are well-defined with regard to essentially any hand or wrist, including both the left hand and right hand.

Regarding the views of the Figures, dorsal views herein refer to views directed toward dorsal sides. For example, a dorsal view of a hand shows the dorsal side of the hand, which side is sometimes called the back of the hand. Similarly, a radial view of a hand generally would include a showing of the thumb, a volar view of a hand generally would include a showing of the palm, and an ulnar view of a hand generally would include a showing of the fourth finger from the thumb.

Regarding planes and axes, volar-dorsal planes are generally perpendicular to radial-ulnar planes, and the forearm generally defines a longitudinal axis. The reader should consider again the forearm and hand resting palm-side down on a planar desktop, particularly when the hand and forearm are comfortably aligned and the fingers are extended straight and held tightly together. In this disposition of the forearm and hand, the plane of the desktop defines a radial-ulnar plane; a longitudinal axis is defined along the length of the forearm; and the four fingers of the hand extend generally parallel to the longitudinal axis. Furthermore, rotation of a radial-ulnar plane by ninety degrees about the longitudinal axis produces a volar-dorsal plane. For example, when a postcard is slipped between adjacent fingers such that an edge of the postcard abuts the desktop and is held parallel to the longitudinal axis, and such that the postcard stands vertically and ninety degrees from the plane of the desktop, the postcard defines a volar-dorsal plane.

Furthermore, terms of reference such as "phalanx," "phalange," and "interphalangeal joint," which terms are well-known and are found in the prior art, may be used herein with reference to the skeletal anatomy of the human hand. Indeed, descriptions herein of one or more illustrated embodiments of the invention sometimes are made with such terms that may imply that the embodiment is disposed on or abuts the hand. Use of such terms of reference is made herein in order to facilitate an understanding of the invention while the hand and portions thereof are not necessarily considered in such embodiments to be actual elements of the invention.

Nonetheless, for the purpose of interpreting these terms of reference, reference is herein made to the fourth Figure of U.S. Pat. No. 5,676,157 to Kramer, incorporated herein by reference, which issued on Oct. 14, 1997 (the "Kramer patent"). In the fourth Figure of the Kramer patent, the skeletal anatomy of a human hand is illustrated wherein particular bones and joints defined there between are identified. For the purpose of interpreting terms of reference as used herein, the fourth Figure of the Kramer patent may be regarded as a dorsal view of a right hand. As shown and as is commonly known, five digits, including a thumb and four fingers, depend from the hand. The three bones of any one of the four fingers, disposed in increasing distance from the hand, are referred to as: the proximal phalange (or proximal phalanx); the middle phalange (or middle phalanx); and the distal phalange (or distal phalanx). A section of a finger may be referred to herein with regard to a particular phalange without ambiguity in that such a section would include the particular bony phalange and the flesh of the finger about the phalange. For example, in typing or in entering data using a keyboard, distal phalange sections of the fingers generally abut and actuate keys of the keyboard without regard to whether distal phalange bones, which are generally surrounded by the flesh of the fingers, ever directly contact the keyboard.

With regard to joints, for each of the four fingers illustrated in the fourth Figure of the Kramer patent, a proximal interphalangeal (PIP) joint is defined between the proximal phalange and the middle phalange, and a distal interphalangeal (DIP) joint is defined between the middle phalange and the distal phalange. The thumb, however, having less joints than each of the four fingers, generally includes an interphalangeal joint, indicated in the fourth Figure as "THUMB IP," defined between a proximal phalange (or proximal phalanx) and a distal phalange (or distal phalanx). Thus, any recitation herein relating to the "last joint" or "distal joint" of a digit relates equally to any distal interphalangeal joint of a finger and to any interphalangeal joint of a thumb regarding either a left hand or a right hand.

Turning now to the drawings of the present application, splint assemblies in accordance with preferred embodiments of the invention are illustrated and are described in detail below. It should be furthermore understood that the views found in the accompanying drawings relate to splint assemblies for a right forearm, wrist, and hand. Nevertheless, the accompanying drawings and the descriptions herein relate equally as well to splint assemblies for the left forearm, wrist, and hand when a mirror image of the various drawings is considered.

Generally, a splint assembly of preferred embodiments of the invention includes a forearm component, a hand component, and a strut that is configured to span the wrist and connect together the forearm component and the hand component. Each splint assembly also includes one or more straps for securing the splint assembly to a forearm and hand.

Three different preferred splint assemblies 110,210,310, and some variations thereof, are now described in detail and, in methods of preferred embodiments of the invention, the three different splint assemblies 110,210,310 are used in a progressive sequence for treating certain impairments of the hand, as further described in detail below. The three splint assemblies 110,210,310 described below include common components, namely, the same forearm component, adjustable hinge, strut, and palm support platform. The three splint assemblies 110,210,310 primarily differ in respect to their respective hand components, each of which may be removably attached to the same palm support platform.

Splint Assembly 110

Figure 2:
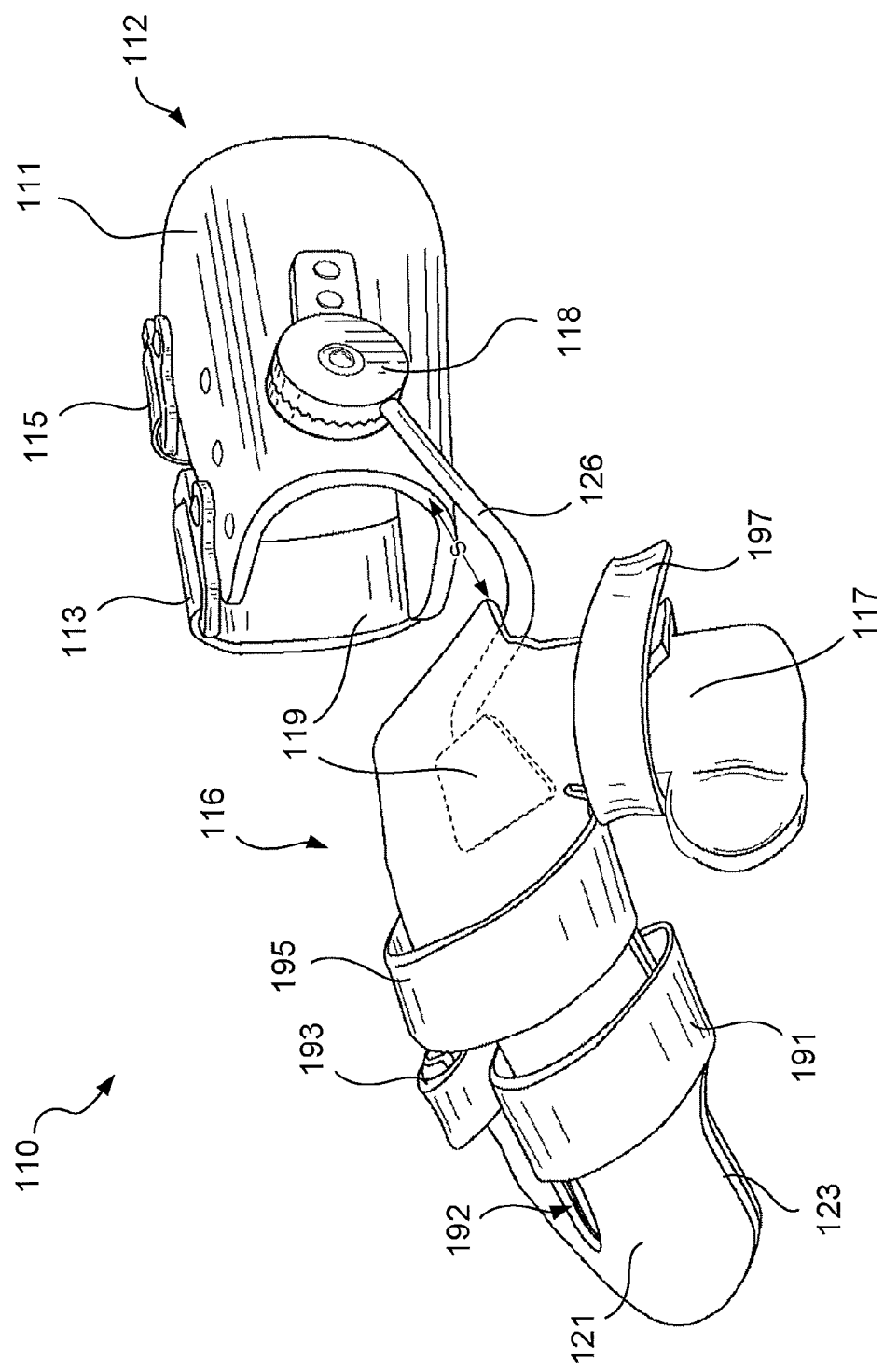
FIG. 2 is a perspective view of the splint assembly 110.
Figure 3:
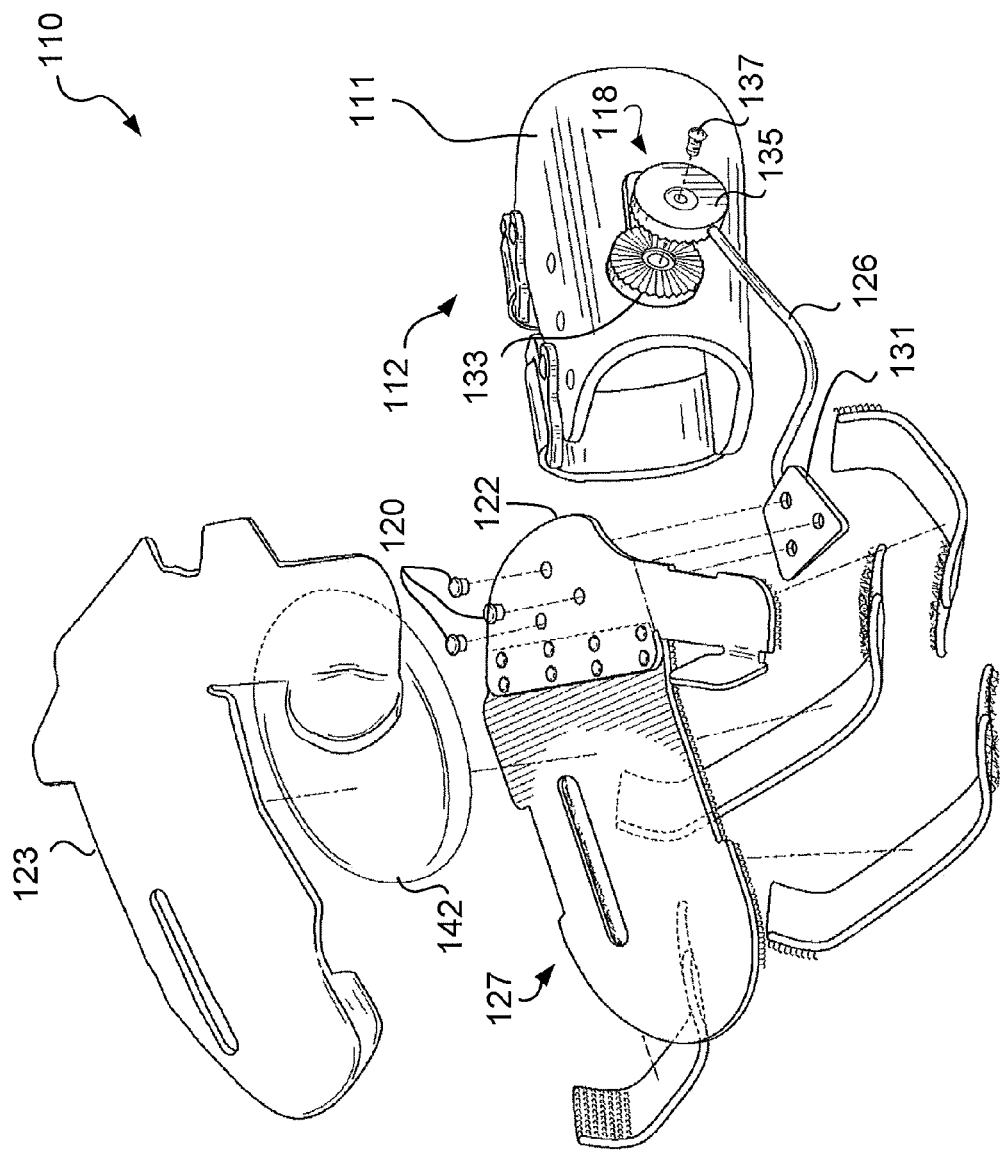
FIG. 3 is an exploded view of the splint assembly 110 shown in FIG. 2.

A perspective view of a first splint assembly 110 in accordance with a preferred embodiment of the invention is shown in FIG. 1. The split assembly 110 is shown being worn on the right hand of a person. The splint assembly 110 is shown by itself in FIG. 2, and an exploded view of the splint assembly 110 is shown in FIG. 3.

The splint assembly 110 includes a forearm component 112 that includes an elongate body 111 having a "C" shaped or "U" shaped cross-section for receiving a forearm therein. The body 111 is configured to be positioned on a forearm such that a distal end thereof is located proximate a person's wrist with the body 111 extending up a person's arm at least several inches. The body 111 generally is static or rigid in nature and preferably is constructed from metal, thermoplastic material, or plastic. The forearm component 112 also includes a pair of straps 113,115 for securing the forearm component 112 on the forearm.

The splint assembly 110 also includes a hand component 116. The hand component 116 includes an outer covering 123 that is padded and that extends over and covers a surface of the hand piece 127 that is configured to abut a volar surface of the hand, which outer covering 123 is perhaps best seen in FIG. 3. In this regard, the outer covering 123 preferably includes hook-and-loop fasteners, and the back side of the hand piece 127 (which back side is not shown in FIG. 3) preferably includes hook-and-loop fasteners for securing the outer covering 123 to the hand piece 127. One or more additional pads 142 further may be utilized in-between the outer covering 123 and hand piece 127.

The hand component 116 includes a general area 117 that is configured to receive and cover, in supporting abutment therewith, the volar surface of the thumb; a general area 119 that is configured to receive and cover, in supporting abutment therewith, the volar surface of the palm; and a general area 121 that is configured to receive and cover, in supporting abutment therewith, the volar surface of digits 2 through 5 of the hand.

The splint assembly 110 further includes a palm support component comprising an adjustable hinge 118, a strut 126, and a palm support platform 131 (all of which are perhaps best seen in FIG. 3). The adjustable hinge 118 comprises mating elements 133,135 and set screw 137. The strut is mounted to element 135 in fixed disposition relative thereto. Mating element 135 is held in fixed disposition against element 133 by tightening set screw 137, which causes mating groves of the elements 133,135 to engage one another in an interlocking relationship. Loosening of the screw 137 allows disengagement of the mating elements 133,135 and rotational adjustment between the mating elements 133,135 along an axis of the set screw 137. The strut 126 extends beyond the distal end of the body 111 of the forearm component 112, with the palm support platform 131 being fixed to the protracting end of the strut 126.

The palm support platform 131 is mounted to the hand component 116 beneath the area 119 of the hand component 116 that is configured to receive, in supporting abutment therewith, a volar surface of the palm of the hand. The palm support platform is mounted to the hand component by extension of fasteners 120 through openings in the palm support platform and corresponding openings in the first section 122 of the hand piece 127 as shown in FIG. 3. Similarly, when the hand piece 177 is used in place of the hand piece 127, the palm support platform is mounted to the hand component 116 by extension of fasteners 120 through openings in the palm support platform and corresponding openings in the first section 182 of the hand piece 177.

The splint assembly 110 also includes straps 191,193,195, 197 for securing the hand component 116 to a hand. Each of the straps preferably includes a non-slip material on a volar side thereof for frictional engagement with the skin of the hand. Each strap also preferably includes hook-and-loop fasteners (as perhaps best seen in FIG. 3), for attachment to itself as well as to hook-and-loop fasteners that may be secured on the back of the hand piece 127 of the hand component 116 (also as perhaps best seen in FIG. 3). As shown in FIG. 1, strap 191 is used to secure the hand component 116 generally to the middle and proximal phalanges of digits 2-4; strap 193 is used to secure the hand component 116 to digit 5; strap 195 is used to secure hand generally in the area of the metacarpals to the hand component 116; and strap 197 is used to secure the hand component 116 to the thumb. Still yet, an additional strap (not shown) for digits 2-4 may be provided and used for securing the hand component 116 generally to the middle and distal phalanges of digits 2-4. Indeed, this additional strap preferably is used, in cases where the patient has increased tone and/or soft tissue shortening, in order to secure the distal ends of digits 2-4. As can be seen in FIGS. 1-3, the hand component 116 defines an elongated opening or slot 192 having an extent that is sufficient for straps 191,193 to concurrently extend there through and, preferably, slot 192 has an extent that is sufficient for the additional strap (not shown) also to concurrently extend therethrough.

Figure 4:
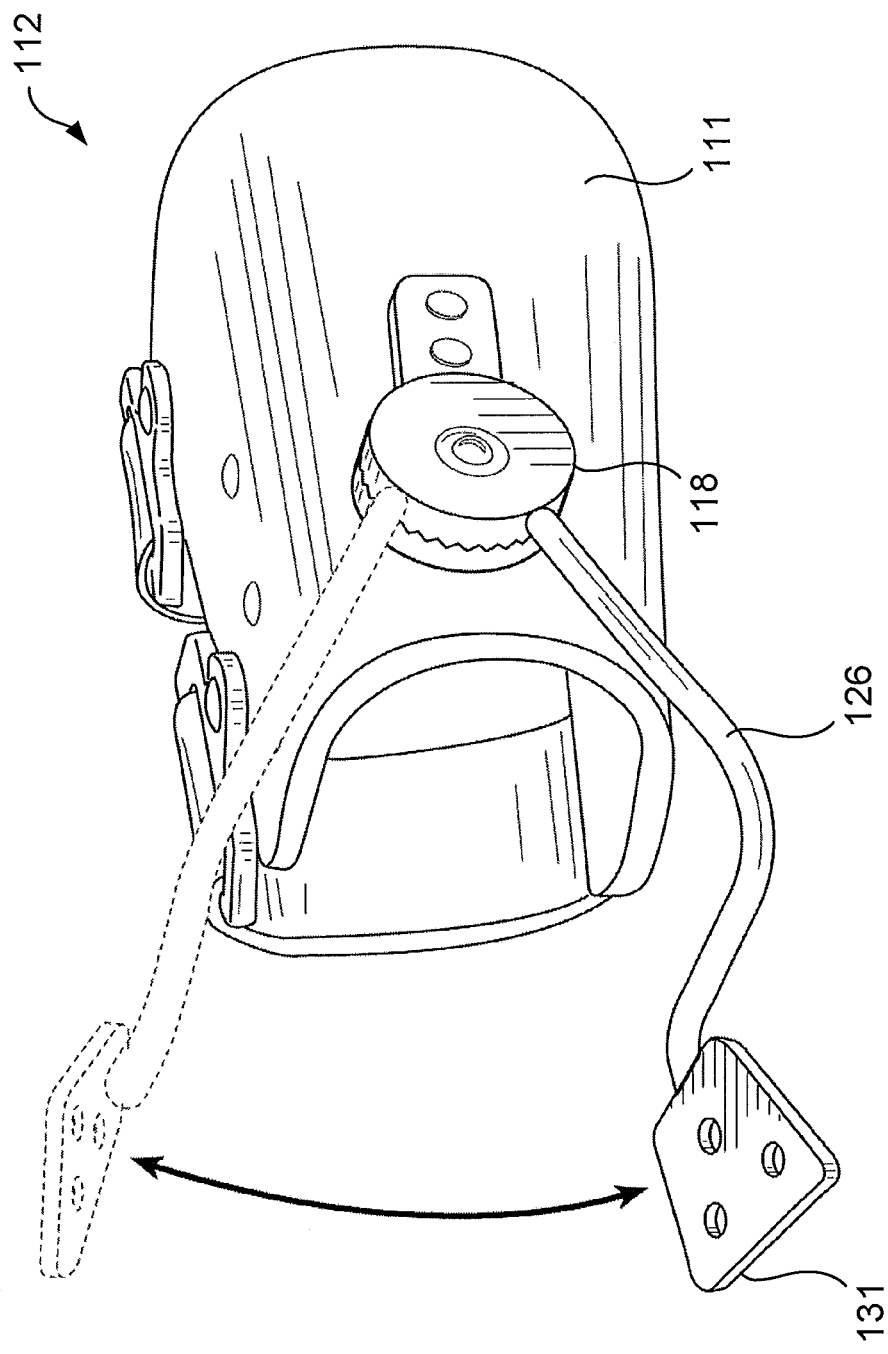
FIG. 4 is a perspective view of the forearm component 112 and palm support component of the splint assembly 110, wherein adjustment of the hinge 118, and resulting adjustment in the relative positioning of the palm support platform 131, are illustrated.

FIG. 4 shows, in further detail, the forearm component 112 and palm support component of the splint assembly 110. As illustrated, the forearm component 112 includes a single strut 126 located on a radial side of the forearm body 111. The hinge 128 is a dynamic hinge and is positioned at an area adjacent the wearer's carpals, where the wrist normally flexes or extends, when the hand splint assembly 110 is worn. Exemplary adjustment of the hinge 118 and the resulting adjustment in the position of the palm support platform 131 relative to the forearm body 111 also are illustrated in FIG. 4.

The palm support component couples the hand component 116 and the forearm component 112 and, in particular, the strut 126 extends therebetween and serves to join the hand component 116 and the forearm component 112. Importantly, the strut 126 extends from the forearm component 112 such that a spacing "S" (shown in FIG. 2) is defined between the hand component 116 and the forearm component 112, whereby the strut 126 spans the wrist of the person when the splint assembly 110 is worn.

Figure 5:
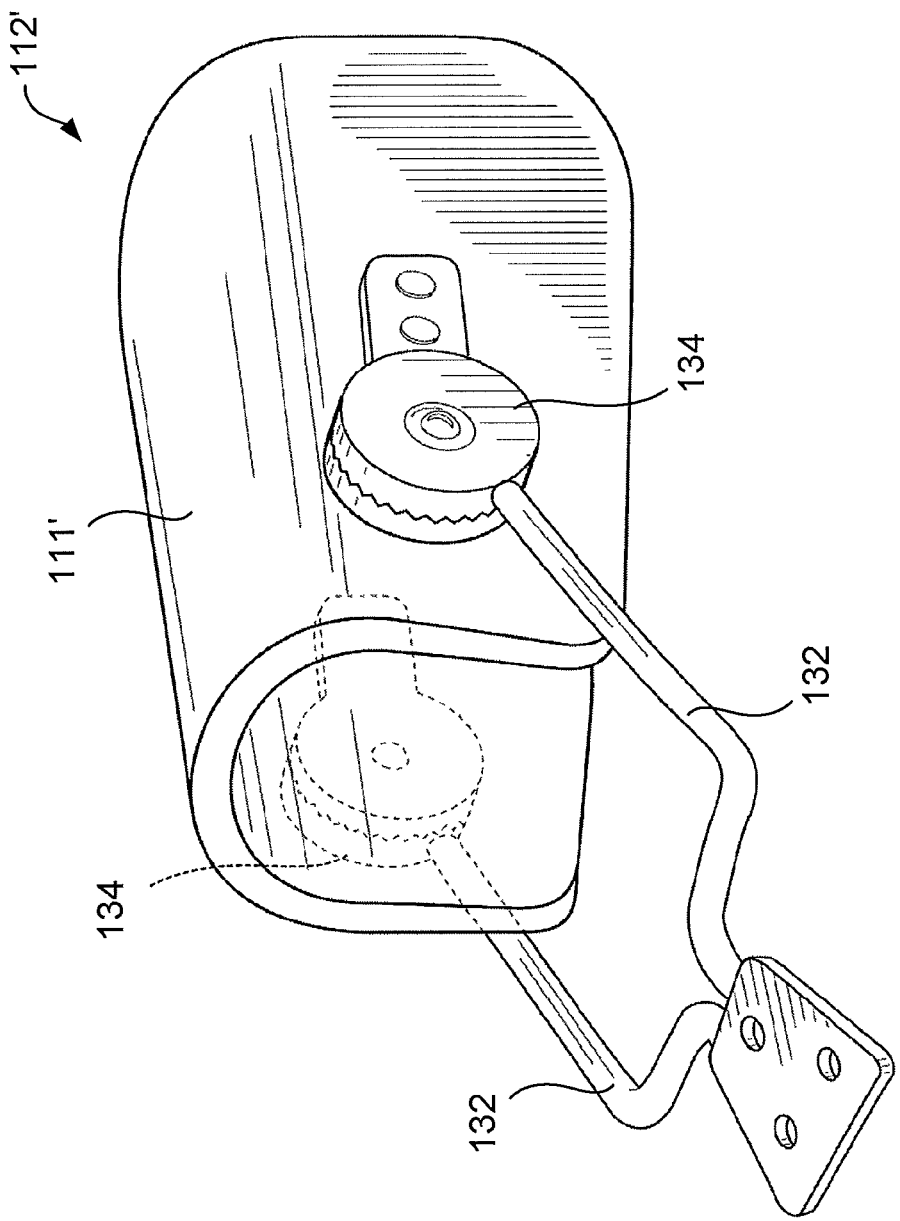
FIG. 5 is a perspective view of an alternative forearm component 112' and palm support component that may be used in each of the splint assemblies 110,210,310.
Figure 6B:
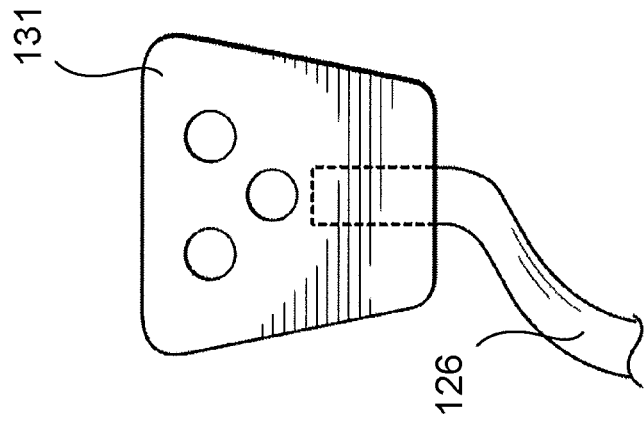
FIG. 6b is a top plan view of a portion of the palm support component of FIG. 4.
Figure 6A:
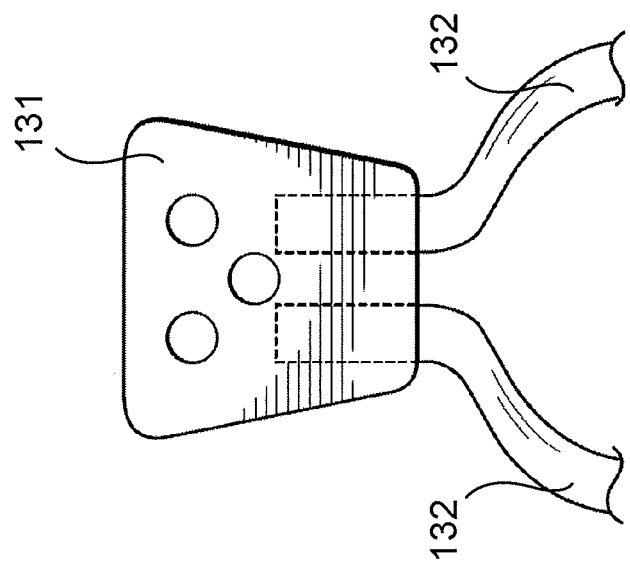
FIG. 6a is a top plan view of a portion of the palm support component of FIG. 5.

FIG. 6 is a perspective view of an alternative forearm component 112' and palm support component that may be used in place of the forearm component 112, wherein the pair of straps have been omitted from the forearm component 112' for clarity. With respect to the modification, the forearm component 112' is orientated with the longitudinal opening for receiving the forearm facing downwardly. The palm support component of the alternative forearm component 112' includes two struts 132 instead of the single strut 126, with one of the struts 132 on the ulnar side of the forearm component 112' and the other of the struts 132 on the radial side of the forearm component 112'. Each strut 132 is coupled to the forearm component 112' by a hinge 134 that is structurally the same as adjustable hinge 118, and each strut 132 extends beyond the distal end of the forearm body 111' such that, when the forearm component 112' is worn, the struts 132 span the wrist. Additionally, the hinges 134 are configured on the forearm body 111' such that, when the forearm component is worn 112', the hinges 134 are located proximate opposite sides of the forearm adjacent the wearer's carpals, where the wrist normally flexes or extends. The protracting ends of the struts 132 converge, whereat palm support platform 131 are mounted on the distal ends thereof as shown in FIG. 5. The converging ends of the struts 132 and palm support platform 131 is further shown in FIG. 6a and, for comparison, the end of the strut 126 and palm support platform 131 is shown in FIG. 6b. The palm support platform is mounted to the strut, for example, by welding or by an adhesive.

It will be appreciated that, in a variation of the alternative forearm component 112' and palm support component shown in FIG. 5, the forearm body 111' equally may be oriented such that the longitudinal opening for receiving the forearm faces upwardly instead of downwardly.

Figure 7A:
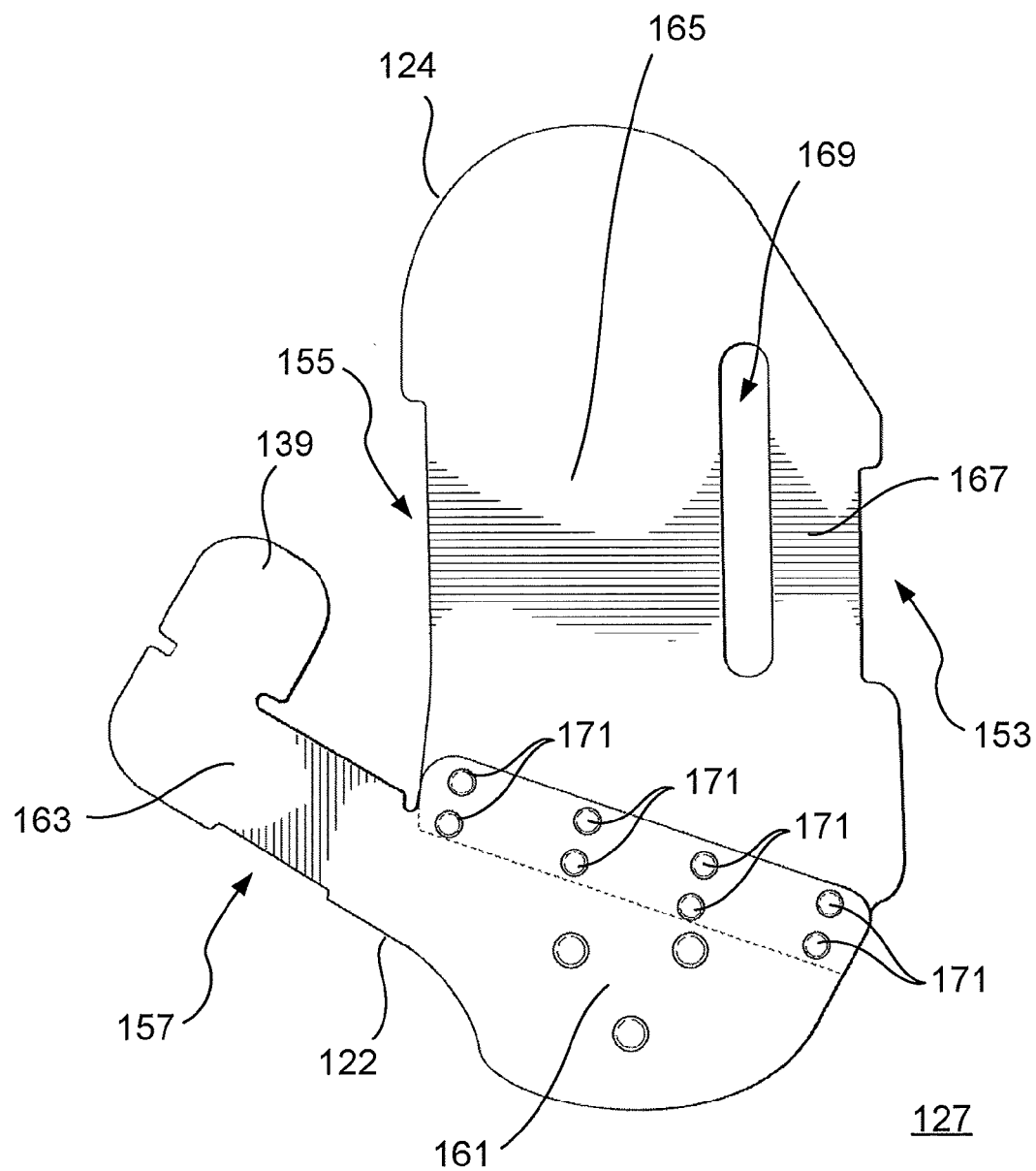
FIG. 7a is a top plan view of components of the hand piece 127 of the splint assembly 110.

FIG. 7a is a top plan view of components of the hand piece 127 of the splint assembly 110 and includes sections constructed of different materials. A first section 122 preferably is constructed from a first material that is malleable so as to be capable of being manually manipulated by hand to position and contour the first material as desired for intimate fit on the hand, but which material is sufficiently rigid so as to be primarily static in nature when the splint assembly 110 is worn. Examples of the first material include, but are not limited to, plastic, metal, fiberglass resin, thermoplastic material, and stainless or cold rolled steel. The first section 122 is configured to abut in an area 161 thereof the volar side of at least a portion of the palm, and is configured to abut, in another area 163 thereof, the volar side of the thumb. The first section 122 further includes a bendable thumb stop 139 that is configured to be bent into a desired position so as to inhibit movement of the thumb toward digits 2-5 beyond a predetermined location when the splint assembly 110 is worn.

The second section 124 preferably is constructed from a second material that is made of an energy storing material (e.g., an elastic or spring-like material that permits bending and provides a restoring force when bent). Examples include, but are not limited to, plastic, fiberglass resins, or spring steel. The energy storing material of the second section 124 allows digits 2-5 of the hands and the joints thereof (MCP, PIP, and DIP) to move through flexion as the hand moves into a flexed or fisted position (resulting from tone, spasticity, and postural changes) and then be urged back into an extended position by the energy storing properties of the material. The second section 124 is configured to abut in an area 165 thereof the volar side of digits 2-4 of the hand, and is configured to abut in an area 167 thereof, the volar side of digit 5 of the hand, with the areas 165,167 being separated by elongate opening 169.

The first section 122 and second section 124 are secured to one another at overlapping portions thereof by fasteners 171. The first section 122 and second section 124 preferably are removably secured such that the fasteners 171 may be detached, the first section 122 and second section 124 separated and, thereafter, reattached. This permits interchanging of the second section 124 with a similarly shaped section having noticeably different energy storing characteristics (e.g., greater or lesser elastic resiliency), whereby greater or lesser restoring forces are provided upon flexion of digits 2-5 of the hand.

To the extent that the hand piece 127 includes two sections of the recited two different materials, the splint assembly 110 of the present invention is similar to the splint assemblies of the incorporated disclosure of WO/2006/072068, and descriptions and variations thereof are adopted herein and applicable to the hand piece 127 described herein. Notable differences between the splint assemblies of this incorporated reference and the splint assembly 110 of the present invention include that the hand piece 116 not being configured to span the wrist, i.e., neither the two sections 122,124 constitutes just the hand piece 127, and that neither section 122,124 forms part of a forearm section or forearm component as in this incorporated reference.

With additional reference to FIG. 7a, the hand piece 127 defines cutouts or indentations along a periphery thereof, which are used to retain straps of the hand component 116 in proper positioning. In this respect, the resilient second section 124 defines an indentation 153 (defined by a "cutout" made in the section 124) along an ulnar side of the hand piece 127 for receipt and retention of the strap 193 when extended through the slot 192 and wrapped around the ulnar side of the hand component, as shown in FIG. 2. Furthermore, the first and second sections 122,124 together define, when secured together, an indentation 155 along a radial side of the hand piece 127 for receipt and retention of the strap 191 when extended through the slot 192 and wrapped around the radial side of the hand component 116, also as shown in FIG. 2. This indentation 155 also receives the strap 195 as well as the additional strap, when used, for securing the hand component 116 to the distal portions of digits 2 through 5 of the hand, as described above. Also, the malleable first section 122 defines, in the area proximal to the IP joint of the thumb, an indentation 157 for receipt and retention of the strap 197 when wrapped around the hand component 116, as shown in FIG. 2. In respect to the foregoing, it will be appreciated that, when the outer covering 123 is applied in covering relation to the hand piece 127, indentations or recesses are formed in the outer covering 123 where the outer covering overlies the indentations 153,155,157, whereby these indentations 153, 155,157 receive and tend to retain the straps in tensioned strapping of the hand component 116 to the hand.

Figure 7B:
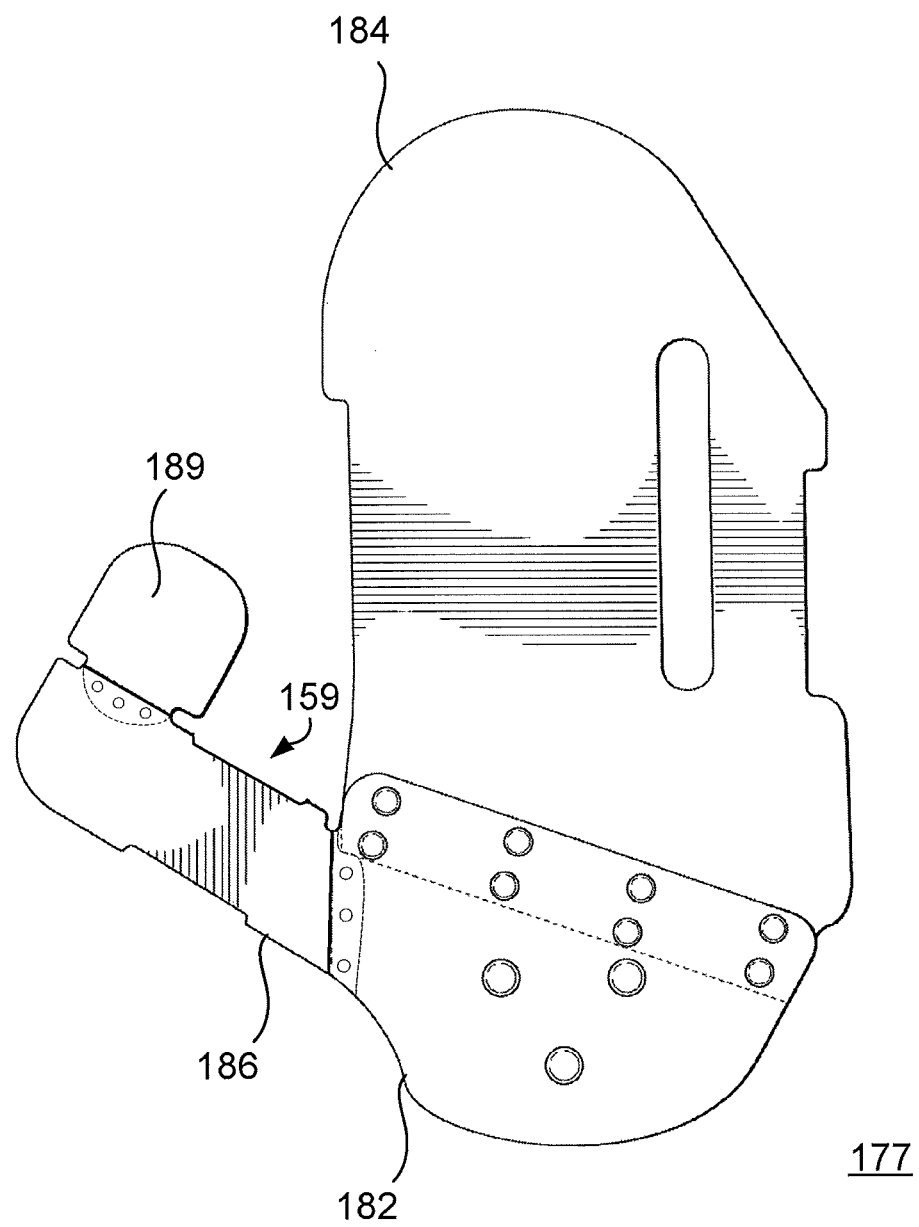
FIG. 7b is a top plan view of components of an alternative hand piece 177 of the splint assembly 110.

FIG. 7b is a top plan view of components of an alternative hand piece 177 that may be used in the splint assembly 110 in substitution for the hand piece 127. Like the hand piece 127, the hand piece 177 includes a first section 182 that is constructed from a first material that is malleable so as to be capable of being manually manipulated by hand to position and contour the first material as desired for intimate fit on the hand, but which material is sufficiently rigid so as to be primarily static in nature when the splint assembly is worn. Examples of the first material include, but are not limited to, plastic, metal, fiberglass resin, thermoplastic material, and stainless or cold rolled steel. The first section 182 is configured to abut the volar side of at least a portion of the palm.

Also like the hand piece 127, the hand piece 177 further includes a second section 184 that is constructed from a second material that is made of an energy storing material (e.g., an elastic or spring-like material that permits bending and provides a restoring force when bent). Examples include, but are not limited to, plastic, fiberglass resins, or spring steel. The energy storing material of the second section 184 allows digits 2-5 of the hands and the joints thereof (MCP, PIP, and DIP) to move through flexion as the hand moves into a flexed or fisted position (resulting from tone, spasticity, and postural changes) and then be urged back into an extended position by the energy storing properties of the material. The second section 184 is configured to abut the volar side of digits 2-5 of the hand.

Furthermore, the first section 182 and second section 184 are removably secured to one another at overlapping portions thereof by fasteners.

Unlike the hand piece 127, the hand piece 177 includes a third section 186 that is removably fastened to the first section 182. The third section is configured to abut the volar side of the thumb. The third section 186 is constructed from a material similar to that of the second section 184, i.e., an energy storing material (e.g., an elastic or spring-like material that permits bending and provides a restoring force when bent). The energy storing material of the third section 186 allows the thumb and joints thereof to move through flexion as the hand moves into a flexed or fisted position (resulting from tone, spasticity, and postural changes) and then be urged back into an extended position by the energy storing properties of the material of the third section 186. The third section 186 preferably begins proximate the MCP joint of the thumb and extends a sufficient length to protract beyond the tip of the thumb.

The first section 182 and third section 186 preferably are removably secured such that the fasteners may be detached, the first section 182 and third section 186 separated and, thereafter, reattached. This permits interchanging of the third section 186 with a similarly shaped section having noticeably different energy storing characteristics (e.g., greater or lesser elastic resiliency), whereby greater or lesser restoring forces are provided upon flexion of the thumb.

The hand piece 177 also includes a fourth section 189 comprising a bendable thumb stop that is constructed from a malleable material and is configured to be bent into a desired position so as to inhibit movement of the thumb toward digits 2-5 beyond a predetermined location when a splint assembly is worn. This fourth section 189 preferably is removably secured by fasteners to the third section 186 and may be detached and reattached to another interchangeable section that may be substituted for the third section 186.

With additional reference to FIG. 7b, the hand piece 184 defines indentations along a periphery thereof like hand piece 127. Additionally, the third section 186 defines an additional indentation 159 proximal to the IP joint of the thumb for receiving and retaining strap 197.

In variations in accordance with the invention, either of the hand pieces 127,177 may or may not include one or more of the aforementioned indentations. Furthermore, one or more of the aforementioned straps may be omitted, and the slot in each hand component (and the slot in each hand piece), may be omitted. Additionally, the third section 186 may be malleable or rigid such that it is not adjustable. The third section 186 additionally may be adjustable between proximal positions and distal positions by disengagement and reattachment of the fasteners to the first section 182.

Splint Assembly 210

Figure 8:
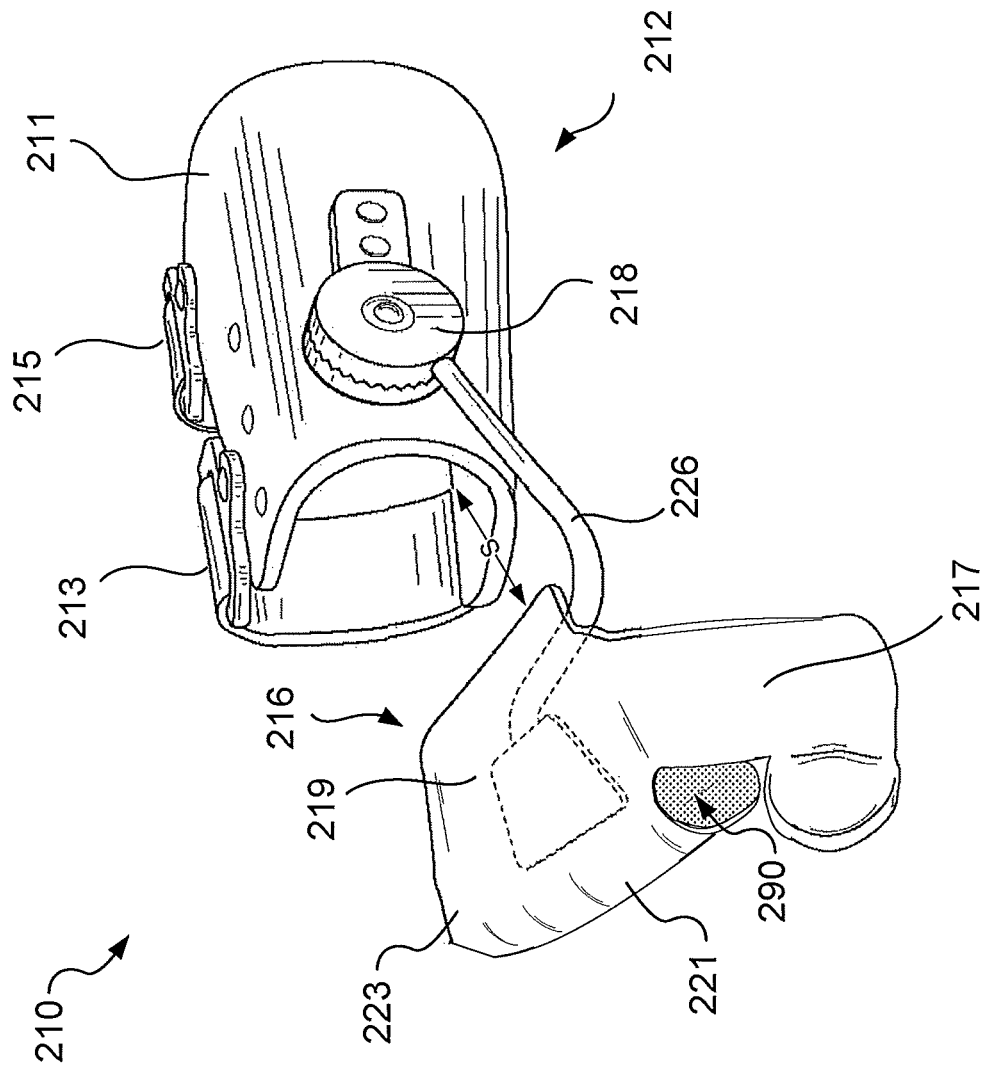
FIG. 8 is a perspective view of a splint assembly 210 in accordance with another preferred embodiment of the invention.
Figure 9:
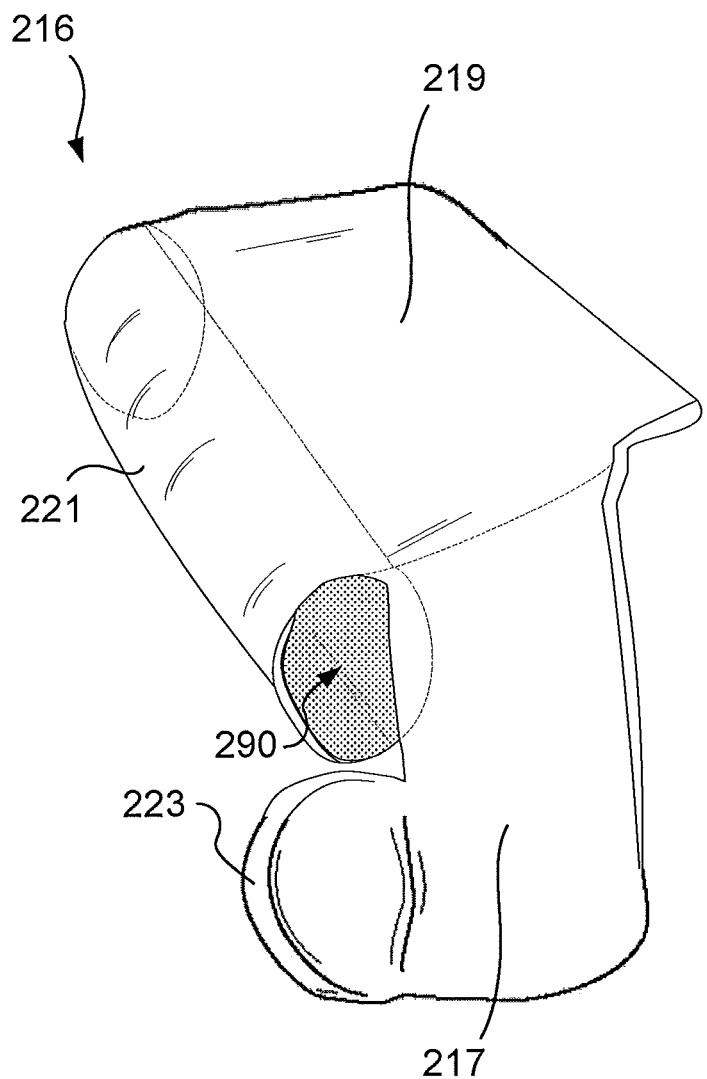
FIG. 9 is a perspective view of the hand component 216 of the splint assembly 210.
Figure 10:
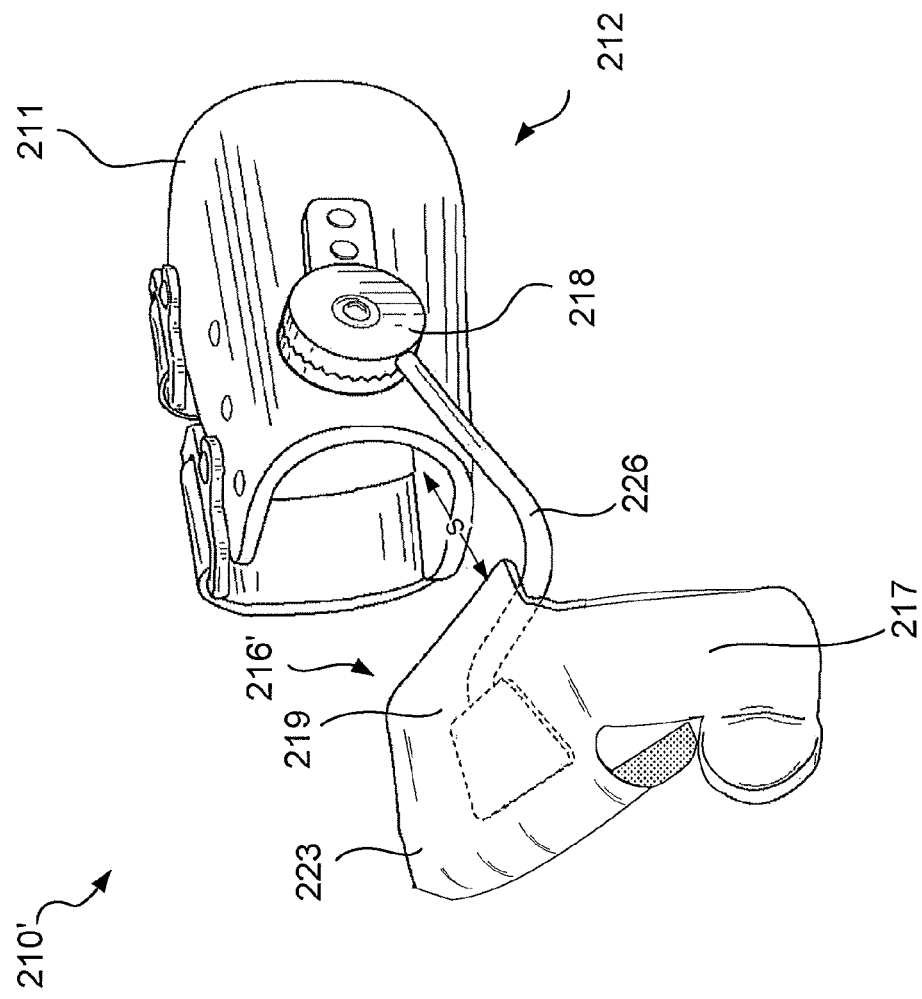
FIG. 10 is a perspective view of a variation of the splint assembly 210'.
Figure 11:
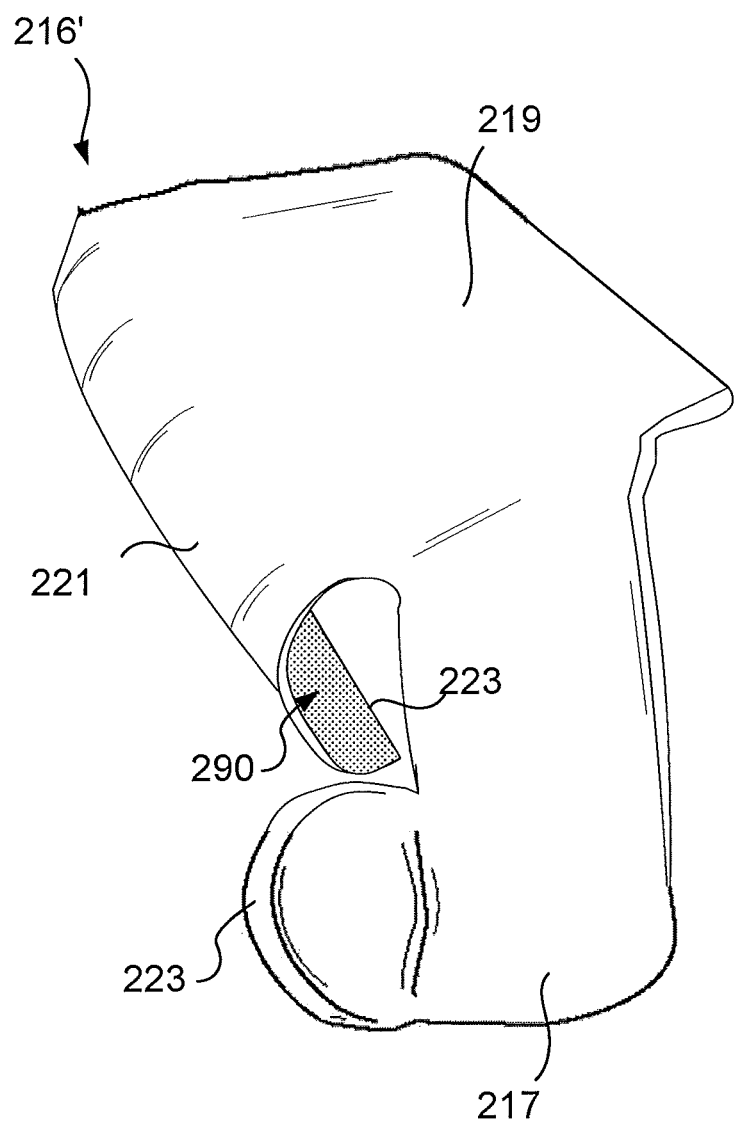
FIG. 11 is a perspective view of the hand component of the variation of the splint assembly 210' of FIG. 10.
Figure 12:
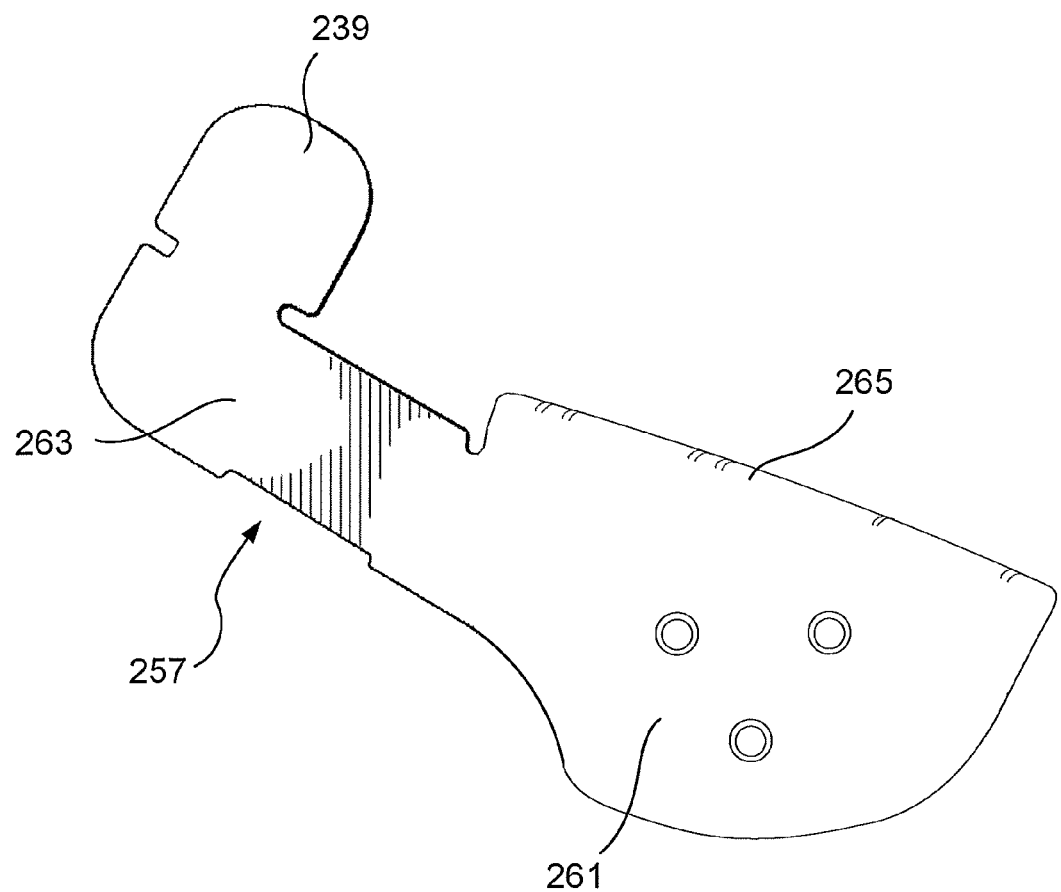
FIG. 12 is a top plan view of a hand piece 227 of the hand component 216 of the splint assembly 210.

A perspective view of a splint assembly 210 in accordance with another preferred embodiment of the invention is shown in FIG. 8. The hand component 216 of the splint assembly 210 is shown in FIG. 9, and a variation of the hand component 216' of the splint assembly 210 is shown in FIGS. 10 and 11. A top plan view of a hand piece 227 of the hand component 216 of the splint assembly 210 is shown in FIG. 12. As will be appreciated, the splint assembly 210 differs from the splint assembly 110 described above principally in the hand component 216.

The splint assembly 210 includes a forearm component 212 that includes an elongate body 211 having a "C" shaped or "U" shaped cross-section for receiving a forearm therein. The body 211 is configured to be positioned on a forearm such that a distal end thereof is located proximate a person's wrist with the body 211 extending up a person's arm at least several inches. The body 211 generally is static or rigid in nature and preferably is constructed from metal, thermoplastic material, or plastic. The forearm component 212 also includes a pair of straps 213,215 for securing the forearm component 212 on the forearm.

The splint assembly 210 also includes a hand component 216. The hand component 216 includes an outer covering 223 that is padded and that extends over and covers a surface of a hand piece 227 of the hand component 216, which hand component is perhaps best seen in FIG. 12. The covering 223 includes hook-and-loop fasteners for attachment to hook-and-loop fasteners located on the back surface of the hand piece 227, as seen for example at 290 in FIG. 8. The hand component 216 includes a general area 217 that is configured to receive and cover, in supporting abutment therewith, the volar surface of the thumb; a general area 219 that is configured to receive and cover, in supporting abutment therewith, the volar surface of the palm; and a generally curved portion 221 that is at least semi-cylindrical and substantially rigid and that is configured to receive and cover, in supporting abutment therewith, the volar surface of digits 2 through 5 of the hand when the hand in a fisted position. Furthermore, as shown in FIG. 9, the generally curved portion 221 is cylindrical, with the end of the curved portion ending proximate or joining with the underside of the general area 219. In this respect, the generally curved portion 221 resembles, and is intended to feel like, a bar when gripped by digits 2-5 of the hand. In a variation, the generally curved portion 221 may terminate along an end edge 223 well before curving back to the underside of the general area 219, such variation being shown in FIGS. 10 and 11. Instead of being rigid, the generally curved portion 221 of the hand piece 210 also may be adjustable. In this respect, a diameter of the generally curved portion 221 (or radius of curvature of the generally curved portion 221) may be increased to provide more of a stretch to the finger flexors, especially as a patient's hand improves with use of the hand splint.

The splint assembly 210 further includes a palm support component comprising an adjustable hinge 218, a strut 226, and a palm support platform. The strut 226 extends beyond the distal end of the body 211 of the forearm component 212, with the palm support platform being fixed to the protracting end of the strut 226.

The palm support platform is mounted to the hand component 216 beneath the area 219 of the hand component 216 that is configured to receive, in supporting abutment therewith, a volar surface of the palm of the hand. The palm support platform is mounted to the hand component by extension of fasteners through openings in the palm support platform and corresponding openings in the hand piece 227.

The splint assembly 210 may include a strap for the thumb as shown, and may include a strap for digits 2-5 of the hand. Any such strap preferably includes a non-slip material on a volar side thereof for frictional engagement with the skin of the hand, and also preferably includes hook-and-loop fasteners for attachment to itself as well as to hook-and-loop fasteners that may be secured on the back of the hand piece 227, partially shown at 290.

The palm support component couples the hand component 216 and the forearm component 212 and, in particular, the strut 226 extends therebetween and serves to join the hand component 216 and the forearm component 212. Importantly, the strut 226 extends from the forearm component 212 such that a spacing "S" (shown, for example, in FIG. 10 and FIG. 12) is defined between the respective hand component 216, 216' and the forearm component 212, whereby the strut 226 spans the wrist of the person when the respective splint assembly 210,210' is worn.

A top plan view of a hand piece 227 which view is representative of both hand components 216,216' is shown in FIG. 12. The hand piece 227 as shown preferably is constructed from a single piece 222 of material. The material preferably is malleable such that the hand piece 227 is capable of being manually manipulated by hand to position and contour the hand piece 227 as desired for intimate fit on the hand. The hand piece 227 further is sufficiently rigid such that it is primarily static in nature when the splint assembly 110 is worn. Examples of such a material include, but are not limited to, plastic, metal, fiberglass resin, thermoplastic material, and stainless or cold rolled steel.

The hand piece 227 is configured to abut in an area 265 thereof the volar side of digits 2-5 of the hand. The hand piece 227 also is configured to abut in an area 261 thereof the volar side of at least a portion of the palm, and is configured to abut in another area 263 thereof the volar side of the thumb.

The hand piece 227 further includes a bendable thumb stop 239 that is configured to be bent into a desired position so as to inhibit movement of the thumb toward digits 2-5 beyond a predetermined location when the splint assembly 210 is worn.

With additional reference to FIG. 12, the hand piece 227 defines an indentation 257 along a periphery thereof in the area proximal to the IP joint of the thumb for receipt and retention of a thumb strap if utilized.

Splint Assembly 310

Figure 13:
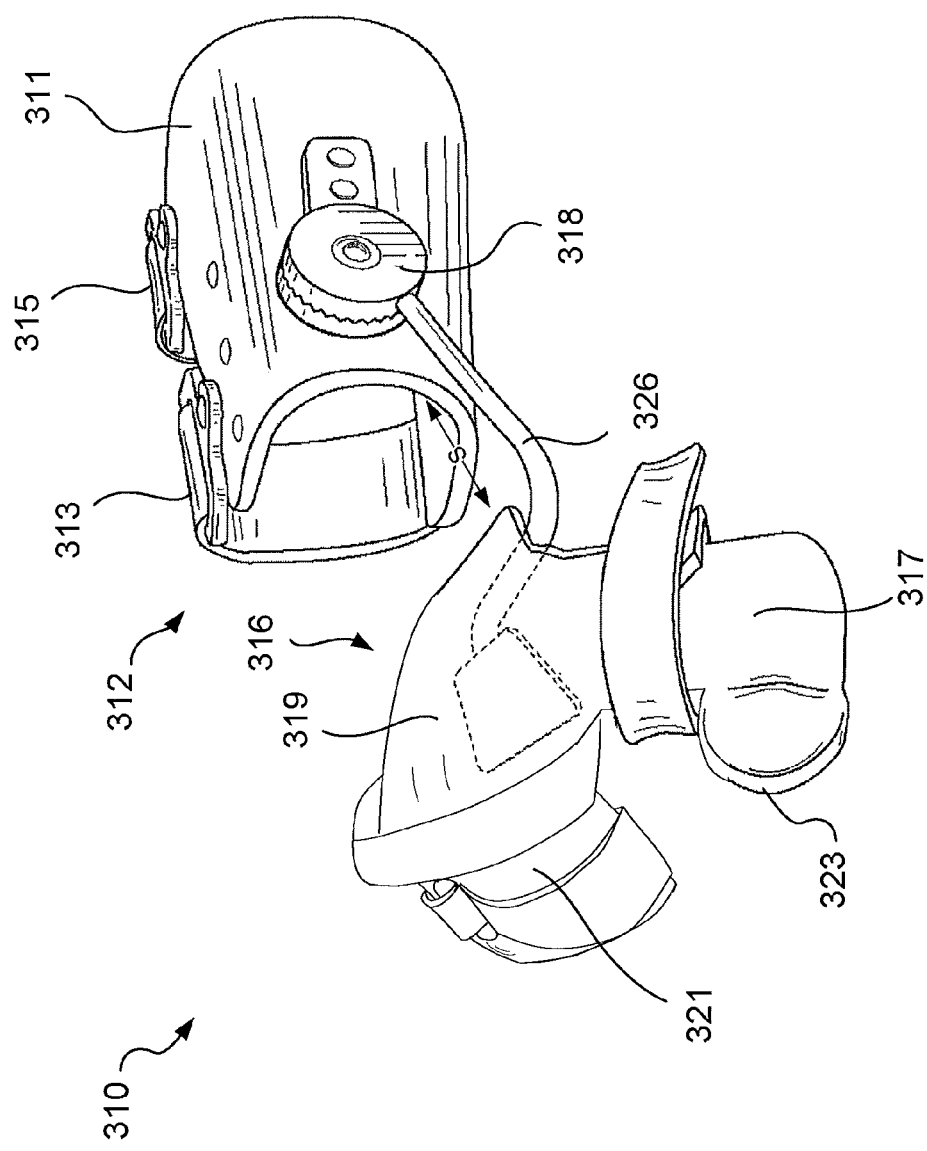
FIG. 13 is a perspective view of a splint assembly 310 in accordance with a third preferred embodiment of the invention.
Figure 14:
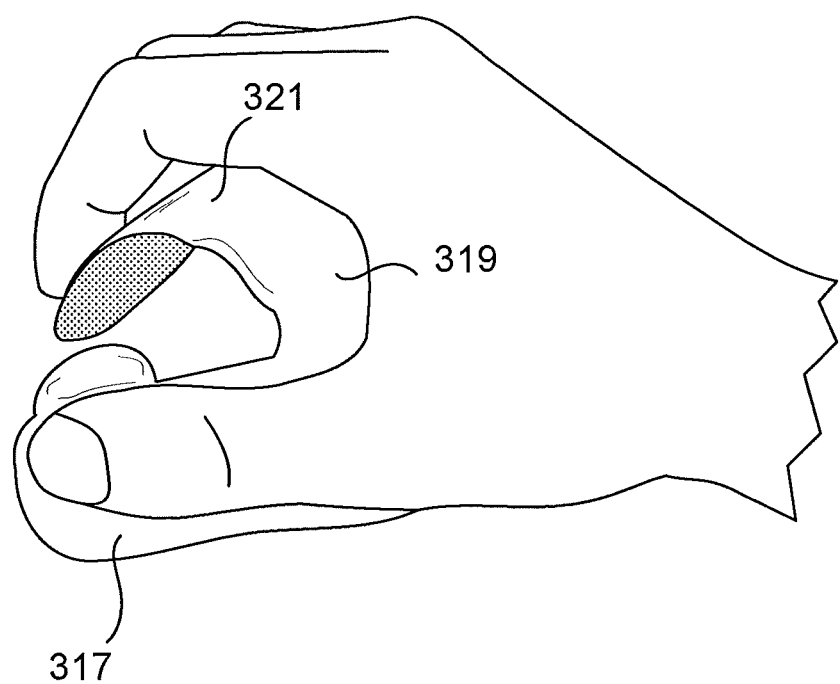
FIG. 14 is a perspective view of the relationship between the hand component 316 of the splint assembly 310 and a hand when the splint assembly 310 is donned.

A perspective view of a splint assembly 310 in accordance with a third preferred embodiment of the invention is shown in FIG. 13. The hand component 316 is shown in FIG. 14 in relation to a hand when the splint assembly 310 is donned. As will be appreciated, the splint assembly 310 differs from the splint assembly 110 described above principally in the hand component 316.

The splint assembly 310 includes a forearm component 312 that includes an elongate body 311 having a "C" shaped or "U" shaped cross-section for receiving a forearm therein. The body 311 is configured to be positioned on a forearm such that a distal end thereof is located proximate a person's wrist with the body 311 extending up a person's arm at least several inches. The body 311 generally is static or rigid in nature and preferably is constructed from metal, thermoplastic material, or plastic. The forearm component 312 also includes a pair of straps 313,315 for securing the forearm component 312 on the forearm.

The splint assembly 310 also includes a hand component 316. The hand component 316 includes an outer covering 323 that is padded and that extends over and covers a surface of a hand piece 327 of the hand component 316, which hand component is perhaps best seen in FIG. 15. The covering 323 includes hook-and-loop fasteners for attachment to hook-and-loop fasteners located on the back surface of the hand piece 327, as seen for example at 390 in FIG. 15. The hand component 316 includes a general area 317 that is configured to receive and cover, in supporting abutment therewith, the volar surface of the thumb; a general area 319 that is configured to receive and cover, in supporting abutment therewith, the volar surface of the palm; and an area 321 that is generally curved and substantially rigid and that is configured to receive and cover, in supporting abutment therewith, the volar surface of digits 2 through 5 of the hand when the hand in an intermediate position. In this respect, the generally curved area 321 is configured to receive in supporting abutment therewith the volar surface of the thumb and the volar surface of digits 2 through 5 of the hand when the hand is in an intermediate position generally midway between a fisted position and a fully open or extended position, the generally curved area 321 of the hand component 316 including a generally curved surface for engagement with digits 2 through 5 when partially flexed in the intermediate position of the hand.

The splint assembly 310 further includes a palm support component comprising an adjustable hinge 318, a strut 326, and a palm support platform. The strut 326 extends beyond the distal end of the body 311 of the forearm component 312, with the palm support platform being fixed to the protracting end of the strut 326.

The palm support platform is mounted to the hand component 316 beneath an area 319 of the hand component 316 that is configured to receive, in supporting abutment therewith, a volar surface of the palm of the hand. The palm support platform is mounted to the hand component by extension of fasteners through openings in the palm support platform and corresponding openings in the hand piece 327.

The splint assembly 310 may include a strap for the thumb, a strap for digits 2-5 of the hand, a strap for digit 5 of the hand, and a strap for the metacarpals. Any such strap preferably includes a non-slip material on a volar side thereof for frictional engagement with the skin of the hand, and preferably includes hook-and-loop fasteners for attachment to itself as well as to hook-and-loop fasteners that may be secured on the back of the hand piece 327, partially shown at 390.

The palm support component couples the hand component 316 and the forearm component 312 and, in particular, the strut 326 extends therebetween and serves to join the hand component 316 and the forearm component 312. Importantly, the strut 326 extends from the forearm component 312 such that a spacing "S" (shown, for example, in FIG. 10 and FIG. 12) is defined between the hand component 316 and the forearm component 312, whereby the strut 326 spans the wrist of the person when the splint assembly 310 is worn.

Figure 15:
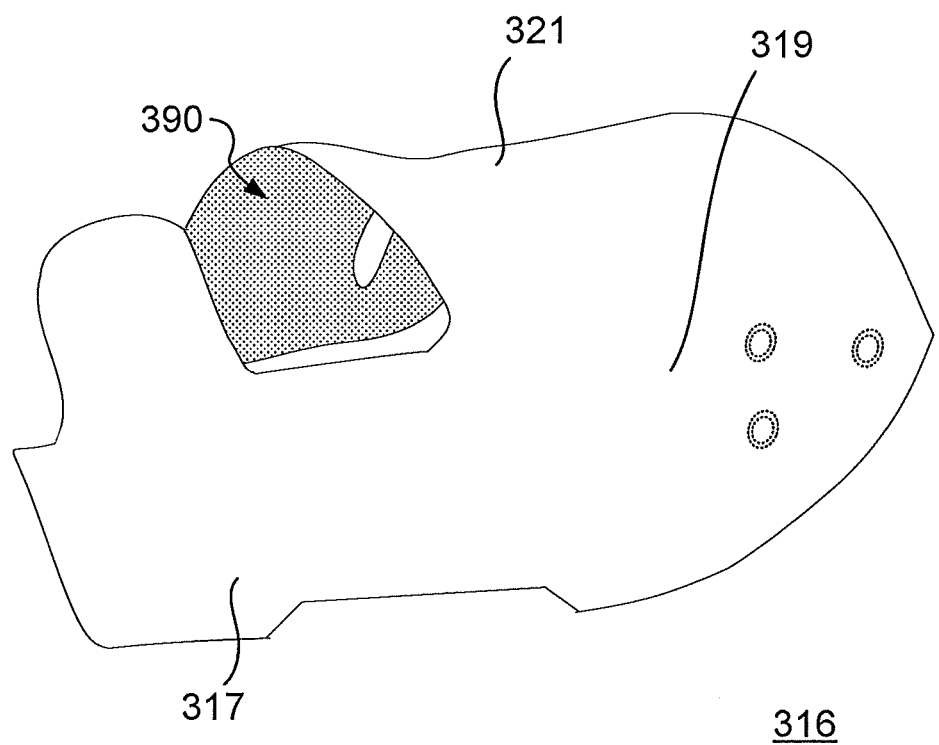
FIG. 15 is a perspective view of the hand component 316 of the splint assembly 310.
Figure 16:
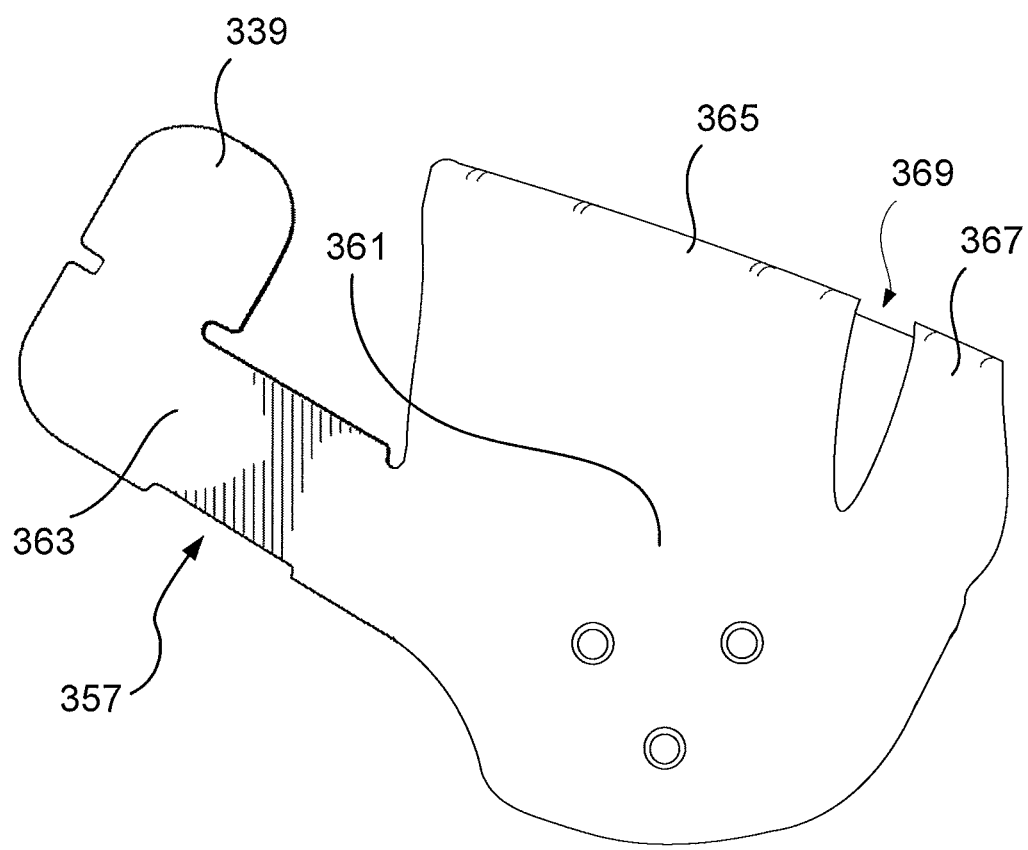
FIG. 16 is a top plan view of the hand piece 327 of the hand component 316 of the splint assembly 310.

A perspective view of the hand component 316 of the splint assembly 310 is shown in FIG. 15, and a top plan view of the hand piece 327 of the hand component 316 of the splint assembly 310 is shown in FIG. 16.

The hand piece 327 as shown preferably is constructed from a single piece of material. The material preferably is malleable such that the hand piece 327 is capable of being manually manipulated by hand to position and contour the hand piece 327 as desired for intimate fit on the hand. The hand piece 327 further is sufficiently rigid such that it is primarily static in nature when the splint assembly 310 is worn. Examples of the such a material include, but are not limited to, plastic, metal, fiberglass resin, thermoplastic material, and stainless or cold rolled steel. The hand piece 327 further includes a bendable thumb stop 339 that is configured to be bent into a desired position so as to inhibit movement of the thumb toward digits 2-5 beyond a predetermined location when the splint assembly 230 is worn. In variations (not illustrated in the drawings), the thumb stop constitutes a separate section of the hand component that is secured by fasteners, similar to the hand piece 177 illustrated in FIG. 7b. Further in this respect, the section may be formed of a malleable material, a resilient material, or a rigid material such that it is not adjustable. The thumb stop additionally may be adjustable between proximal positions and distal positions by reattachment of the fasteners.

The hand piece 327 is configured in an area 365 thereof to abut the volar side of digits 2-4 of the hand, and is configured in an area 367 thereof to abut the volar side of digit 5 of the hand, with the areas 365,367 being separated by elongate opening 369, which slot is configured for receipt therethrough of a plurality of straps if utilized. The hand piece 327 also is configured in an area 361 thereof to abut the volar side of at least a portion of the palm, and is configured to abut in another area 363 thereof the volar side of the thumb.

With additional reference to FIG. 16, the hand piece 327 defines an indentation 357 along a periphery thereof in the area proximal to the IP joint of the thumb for receipt and retention of a thumb strap if utilized.

Progressive Use of the Hand Splint Assemblies 110, 210,310

In methods in accordance with preferred embodiments of the invention, the three different splint assemblies 110,210, 310 are used in a progressive sequence for treating certain impairments of the hand.

For example, a therapist preferably uses the splint assembly 210 on a patient having a hand that tends to be in a fisted position. The rigid bar-like shape of the hand component of the splint assembly 210 accommodates the four fingers, which tend to curl there around. Furthermore, the malleable thumb portion of the hand component of the splint assembly 210 is utilized in positioning the thumb and, thereafter, repositioning the thumb during instances of subsequent use. It will further be appreciated that during any instance of use, the thumb portion will not change positions when the patient's tone kicks in (e.g., when the patient coughs or stands or otherwise exerts himself or herself) because of sufficient rigidity of the thumb portion.

The splint assembly 310 preferably is utilized as the patient's hand and, specifically, the fingers, begin to extend as a result of the use of the splint assembly 210. The splint assembly 310 includes the hand component having a hand piece that is malleable both in the area of support of the digits 2-5 of the hand as well as in the area of support of the thumb and the palm. During progressive sequences of use of the splint assembly 310, the area of support of the digits 2-5 of the hand is progressive straightened from a first curved position, thereby tending to force the patient's fingers into extension as the patient's tone improves. Moreover, during any instance of use, no part of the hand component will bend or flex in response to the patient's tone kicking in due to the sufficient rigidity of the hand component.

The splint assembly 110 is last used once the patient's hand has improved to such extent that a long, sustained stretch is determined to be both practical and beneficial. In this case, during use any flexing of the digits 2-5 is countered by the restoring force of the hand component, which continually applies a stretching force to the digits 2-5 in response to continued flexing of the digits 2-5. Moreover, a similarly restoring force is applied when the thumb portion is dynamic, too. Alternatively, the thumb is positioned and held in such position during an instance of use by a malleable thumb portion, as in the splint assemblies 210,310.

Additionally, it is contemplated that a kit may be provided to the therapist, wherein the kit includes one of the splint assemblies 110,210,310 and the hand components of the other two splint assemblies, whereby the therapist could change out the hand components during the above described progression.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

By way of example, the components of the hand piece 177 in FIG. 7b are shown secured to each other by fasteners. It is contemplated within the scope of the invention that these components may constitute integral sections of the same piece so long as each section exhibits the differing characteristics described herein, including malleability and resiliency. Such could be accomplished through, for example, manufacturing steps including co-molding.

Additionally, thumb stops (whether integral with the remainder of the hand component or constituting separate sections of the hand component) of the afore described hand splints have been disclosed as being malleable and bendable for positioning and repositioning of the stopping location for the thumb. It will further be appreciated that, within the scope of the invention: the thumb stop may not be malleable and, instead, may be rigid and nonadjustable; and additionally or alternatively, the thumb stop may be adjustable relative to the remainder of the hand piece via fasteners (such as shown in FIG. 7b) whereby the position of the thumb stop may be adjusted between proximal positions and distal positions. Such variations may be desirable because some thumbs may be more hypermobile than others and may require more adjustability than simply bending the metal of the thumb stop.

Furthermore, it will be appreciated that any of the forearm components and palm support components disclosed herein may be used with any of the hand components disclosed herein.

What is claimed is:

1. A hand splint comprising:
   (a) a forearm component configured to attach to a person's forearm such that a distal end of the forearm component is located proximate the person's wrist and such that the forearm component extends up the person's arm;
   (b) a hand component including a first portion and a second portion, the hand component configured to receive, in supporting abutment therewith, a volar surface of at least one of a plurality of digits of the person's hand;
   (c) a palm support component coupling together the forearm component and the hand component, the palm support component comprising,
      (i) a palm support platform, and
      (ii) a first strut attached to and coupling together the forearm component and the palm support platform;
   (d) wherein the palm support platform is mounted to the hand component and is configured to receive, in supporting abutment therewith, a volar surface of a palm of the person's hand;
   (e) wherein the first strut extends from the forearm component such that a spacing is defined between the hand component and the forearm component, the first strut spanning the wrist of the person when the hand splint is donned; and
   (f) wherein the second portion of the hand component comprises a resilient material that, in response to bending, such as during flexion of an abutted digit, generates a continuous restoring force in opposition to such bending, whereby the abutted digit in flexion is urged toward extension.

2. The hand splint of claim 1, wherein the first portion of the hand component is comprised of a malleable material such that the second portion of the hand component may be bent for customizing the abutting support of the hand by the hand component.

3. The hand splint of claim 2, wherein the first portion of the hand component is configured to receive the volar surface of the thumb.

4. The hand splint of claim 3, wherein the hand component includes a generally curved, semi-cylindrical portion that is rigid, and wherein the hand component is configured to receive in supporting abutment therewith the volar surface of the thumb and the volar surface of digits 2 through 5 of the hand when the hand is in a fisted position, the generally curved, semi-cylindrical portion receiving in supporting abutment therewith the volar surface of digits 2 through 5 when flexed in the fisted position of the hand.

5. The hand splint of claim 2, wherein the first portion of the hand component is configured to receive the volar surface of the palm of the hand.

6. The hand splint of claim 2, wherein the first portion of the hand component is configured to receive the volar surface of the thumb and the volar surface of the palm of the hand.

7. The hand splint of claim 2, wherein the hand component includes a generally curved portion that is malleable, and wherein the hand component is configured to receive in supporting abutment therewith the volar surface of the thumb and the volar surface of digits 2 through 5 of the hand when the hand is in an intermediate position generally midway between a fisted position and a fully open position, the generally curved portion of the hand component including a generally curved surface for engagement with digits 2 through 5 when partially flexed in the intermediate position of the hand.

8. The hand splint of claim 1, further comprising a first adjustable hinge attached to the forearm component that is configured to be attached to the forearm such that, when the forearm component is attached to the forearm, the first adjustable hinge is located adjacent the person's carpal whereat the wrist normally flexes and extends, wherein the first strut is attached to the first adjustable hinge and the palm support platform.

9. The hand splint of claim 8, further comprising a second strut and a second adjustable hinge mounted to the forearm component, the second strut attached to and coupling together the second adjustable hinge and the palm support platform, the second strut extending on an opposite side of the forearm component relative to the first said strut.

10. The hand splint of claim 1, wherein neither the forearm component nor the hand component is configured to span the wrist when the hand splint is donned.

11. A hand splint comprising:
(a) a forearm component configured to attach to a person's forearm such that a distal end of the forearm component is located proximate the person's wrist and such that the forearm component extends up the person's arm;
(b) a hand component having a first section configured to receive, in supporting abutment therewith, a volar surface of the palm of the hand, and a second section configured to receive, in supporting abutment therewith, a volar surface of digits 2 through 5 of the person's hand;
(c) a strut attached to, and coupling together, the forearm component and the hand component, the strut extending from the forearm component such that a spacing is defined between the hand component and the forearm component, whereby the strut spans the wrist of the person when the hand splint is donned;
(d) wherein the second section of the hand component comprises a resilient material that, in response to bending, such as during flexion of an abutted one of digits 2 through 5 of the hand, generates a continuous restoring force in opposition to such bending, whereby an abutted digit in flexion is urged toward extension; and
(e) wherein the first section of the hand component comprises a malleable material that does not generate, in response to bending, a continuous restoring force in opposition to such bending, whereby the first section is able to be manually shaped for customizing the abutting support of the hand by the second section of the hand component.

12. The hand splint of claim 11, wherein the hand component further comprises a third section configured to receive, in supporting abutment therewith, a volar surface of the thumb of the hand.

13. The hand splint of claim 12, wherein the third section of the hand component comprises a resilient material that, in response to bending, such as during flexion of the thumb, generates a continuous restoring force in opposition to such bending, whereby the abutted thumb in flexion is urged toward extension.

14. The hand splint of claim 13, wherein the first, second and third sections of the hand component are removably secured to one another.

15. A hand splint comprising:
(a) a forearm component configured to attach to a person's forearm such that a distal end of the forearm component is located proximate the person's wrist and such that the forearm component extends up the person's arm;
(b) a hand component having a first section and a second section, the second section being configured to receive, in supporting abutment therewith, a volar surface of digits 2 through 5 of the person's hand;
(c) a first strut attached to and coupling together the forearm component and the hand component, the first strut extending from the forearm component such that a spacing is defined between the hand component and the forearm component, whereby the first strut spans the wrist of the person when the hand splint is donned; and
(d) wherein the second section of the hand component comprises a resilient material that, in response to bending, such as during flexion of an abutted finger, generates a continuous restoring force in opposition to such bending, whereby an abutted finger in flexion is urged toward extension.

16. The hand splint of claim 15, wherein the first section of the hand component is configured to receive, in supporting abutment therewith, a volar surface of both the palm and thumb of the hand, the first and second sections being removably secured to one another, and the first section of the hand component comprises a malleable material that does not generate, in response to bending, a continuous restoring force in opposition to such bending, whereby the first section is able to be manually shaped for customizing the abutting support of the hand by the second section of the hand component.

17. The hand splint of claim 15, further comprising a second strut and an adjustable hinge mounted to the forearm component, the second strut attached to and coupling together the adjustable hinge and the palm support platform, the second strut extending on an opposite side of the forearm component relative to the first strut.

18. The hand splint of claim 15, wherein the second section of the hand component is configured to abut the volar side of the length of at least one of digits 2 through 5.

19. The hand splint of claim 15, wherein the second section is releasably connected to the first section.

20. The hand splint of claim 15, further comprising a plurality of straps for securing the hand component to a hand, and wherein the second section of the hand component defines a slot having an extent sufficient for three of the straps to concurrently extend there through.

* * * * *